(12) United States Patent
Maas

(10) Patent No.: US 6,440,094 B1
(45) Date of Patent: Aug. 27, 2002

(54) ORTHOPEDIC GARMENT FOR DYNAMICALLY ENHANCING PROPER POSTURE

(76) Inventor: Richard D. Maas, 1264 Tennessee Rd., Ozark, MO (US) 65721

( * ) Notice: Subject to any disclaimer, the term of this patent is extended or adjusted under 35 U.S.C. 154(b) by 0 days.

(21) Appl. No.: 09/478,187

(22) Filed: Jan. 5, 2000

Related U.S. Application Data

(60) Provisional application No. 60/168,115, filed on Nov. 30, 1999.

(51) Int. Cl.$^7$ .................................................. A61F 5/00
(52) U.S. Cl. ................. 602/5; 602/4; 602/19; 602/20; 2/44
(58) Field of Search ............... 602/50, 62, 4, 602/20, 19, 5, 61; 2/455

(56) References Cited

U.S. PATENT DOCUMENTS 5,628,725 A * 5/1997 Ostergard ............... 602/20
5,857,990 A * 1/1999 Maas ....................... 602/20

OTHER PUBLICATIONS

Product specification sheet of The Saunders Group, Inc., Chaska, Minnesota, for two products entitled (i) "Saunders Posture S'port" and (ii) "Posture Corrector." Circa, 1996.

* cited by examiner

Primary Examiner—John G. Weiss
Assistant Examiner—Linh Truong
(74) Attorney, Agent, or Firm—Jonathan A. Bay

(57) ABSTRACT

An orthopedic method for dynamically enhancing proper posture utilizes an elastic base garment and halter strap system. The base garment is generally collarless and sleeveless, as a stocking-like tube interconnecting a pair of shoulder pads and a waist band, which have hook-fastener securing areas. Correspondingly, the elastic halters have hook-fastener tag ends. The halter's hook fasteners are secured to the base garment's hook-fastener securing areas such that one halter supplies tension between an origin on the right shoulder pad and a termination on the waist band approximately on the left side, as the other halter supplies tension between an origin on the left shoulder pad and another termination on the waist band approximately on the right side, by courses stretching diagonally across the garment's back. Thus the halters provide diagonally-crossing filaments of tension across the patient's back in order to oppose slouching and thereby enhance proper erect posture.

20 Claims, 16 Drawing Sheets

(Front)

(Rear)

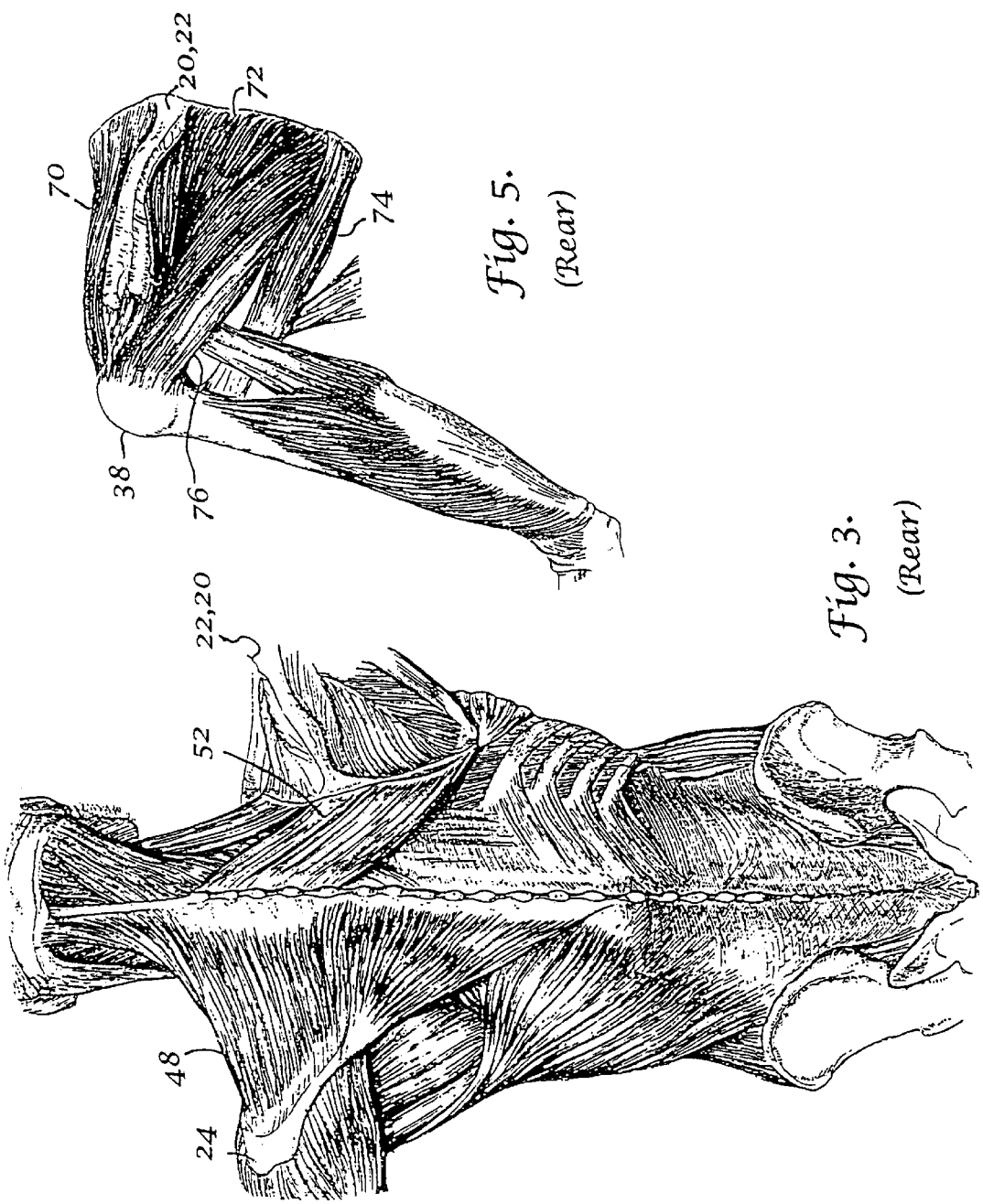

(Front)

(Front)

(Front)

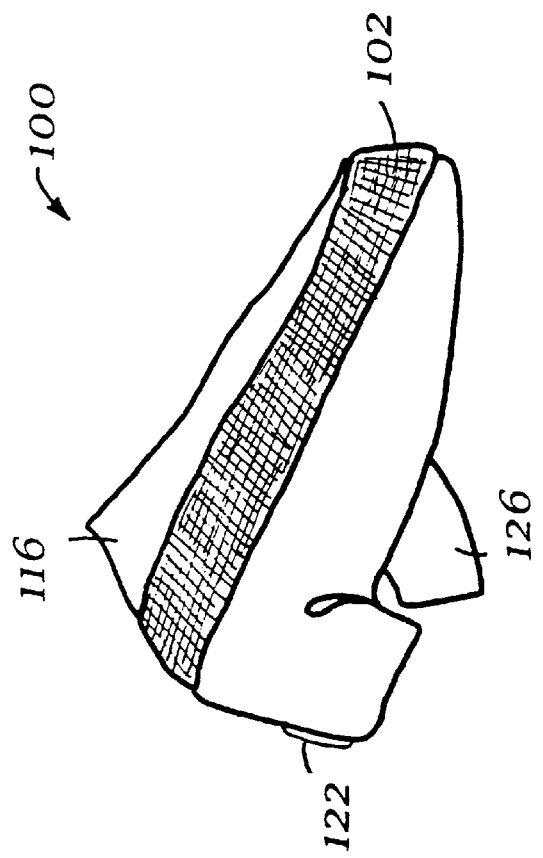
Fig. 8b. (Rear)
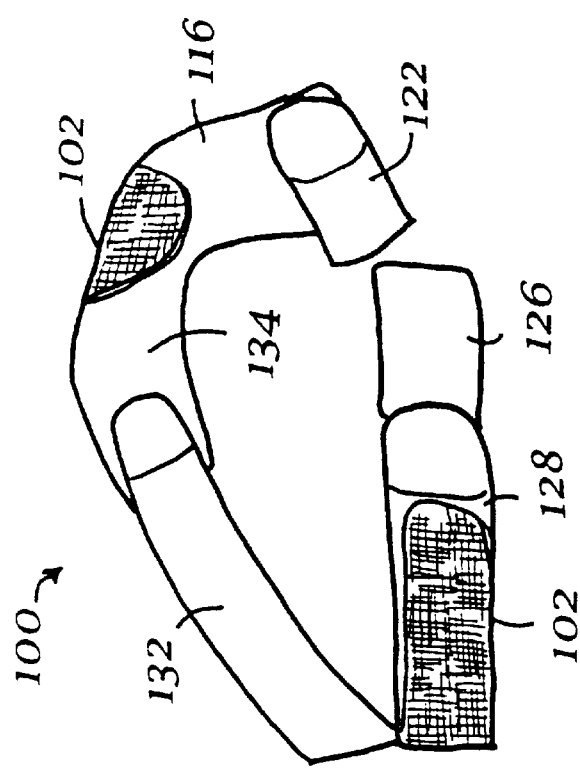
Fig. 8a. (Front)

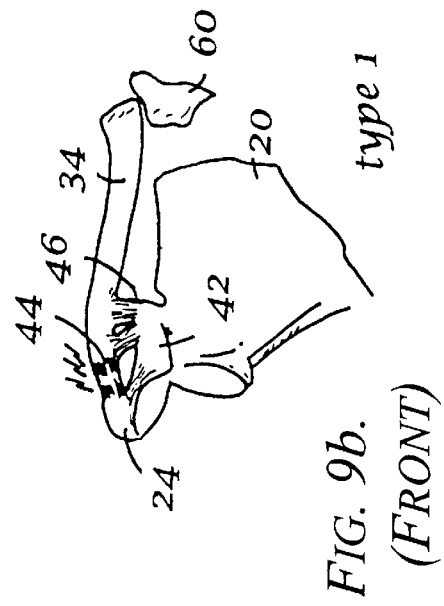
FIG. 9a. (FRONT) normal
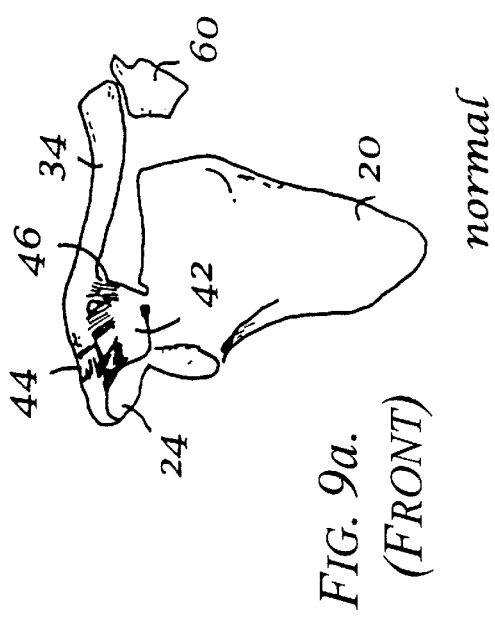
FIG. 9b. (FRONT) type I
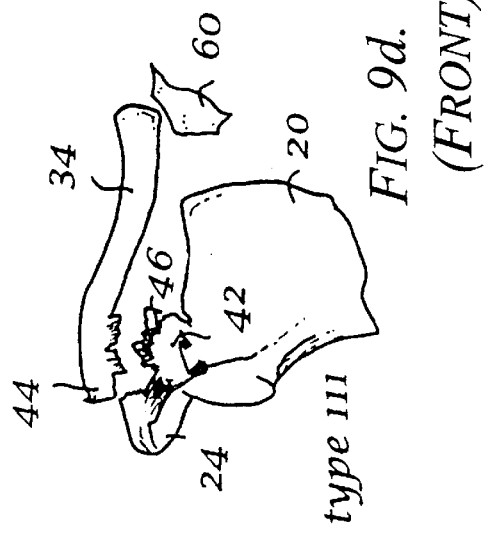
FIG. 9c. (FRONT) type II
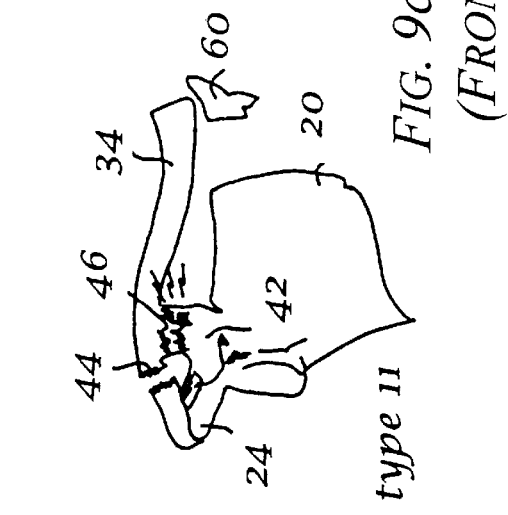
FIG. 9d. (FRONT) type III

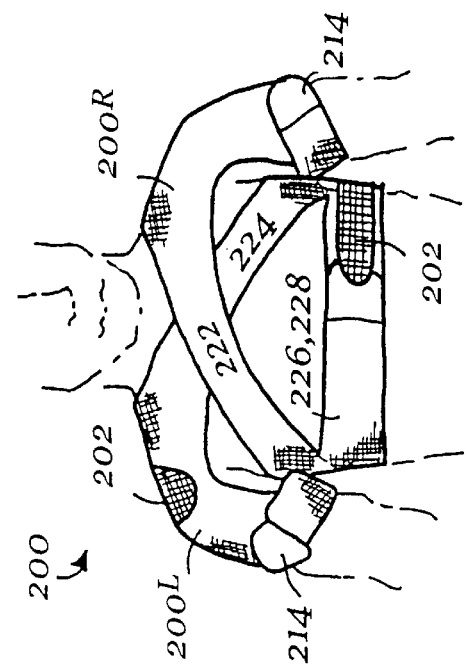
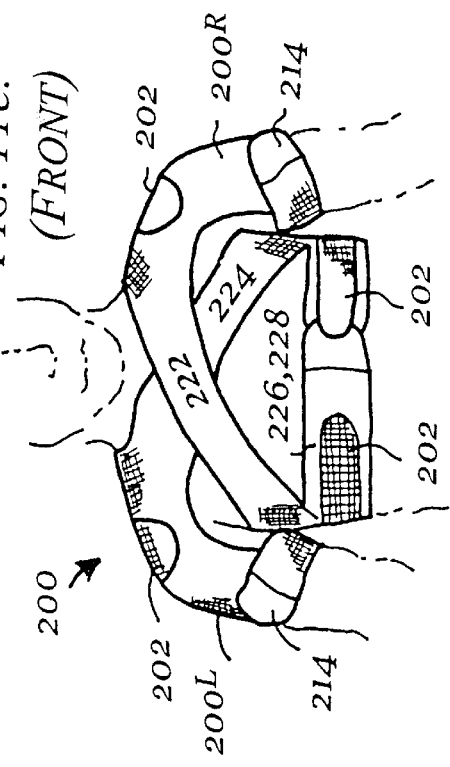
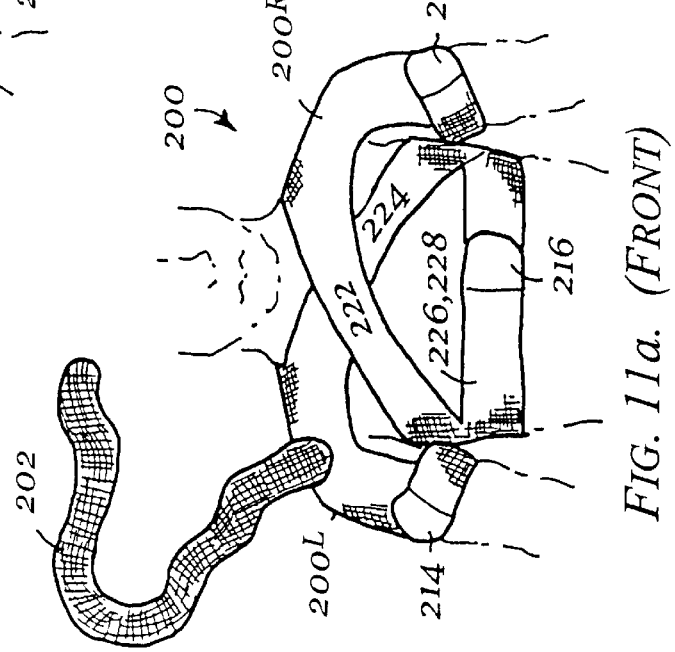

(REAR)

(REAR)

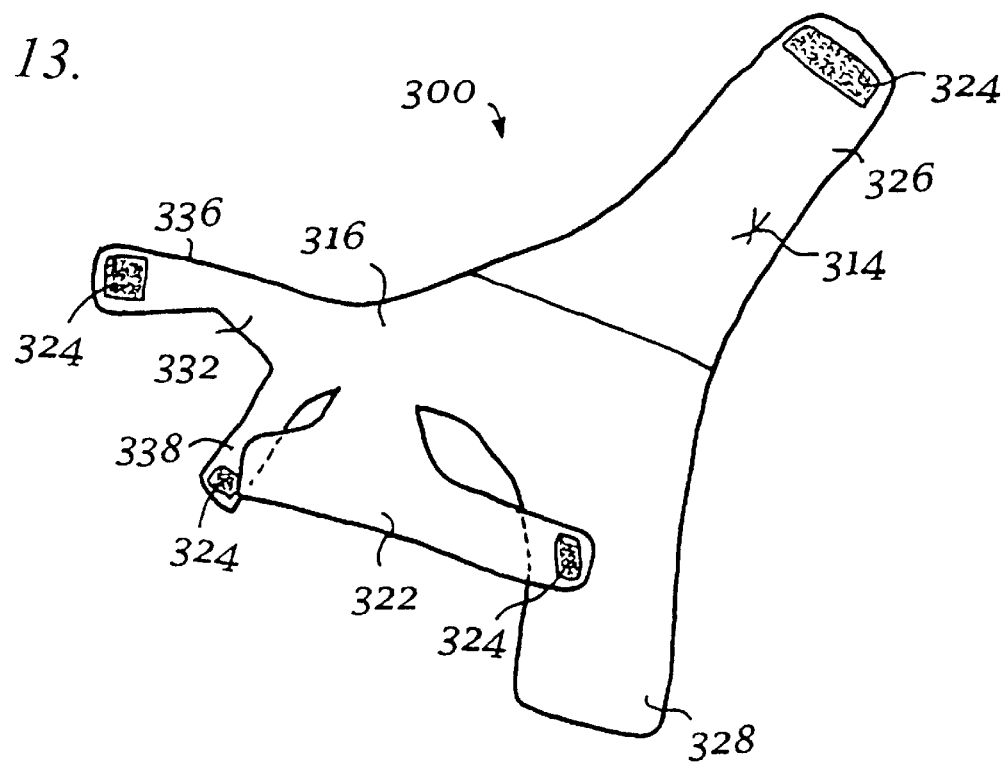
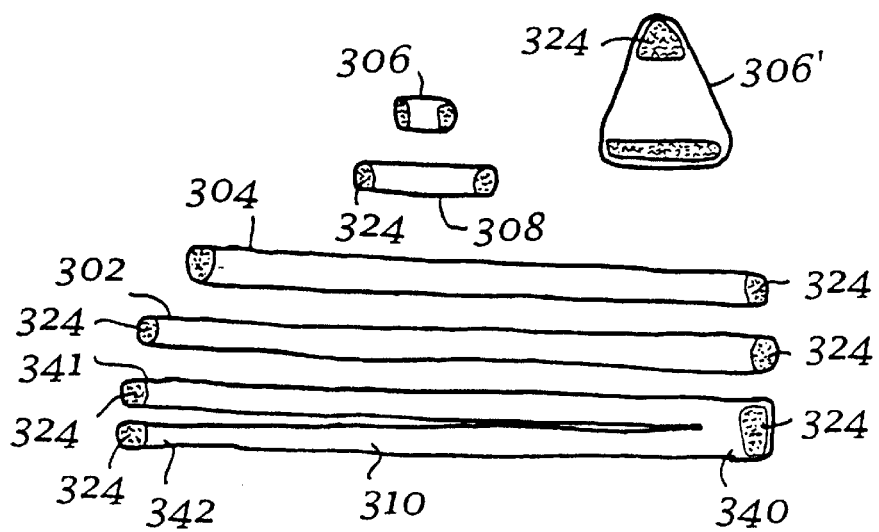
FIG. 13.

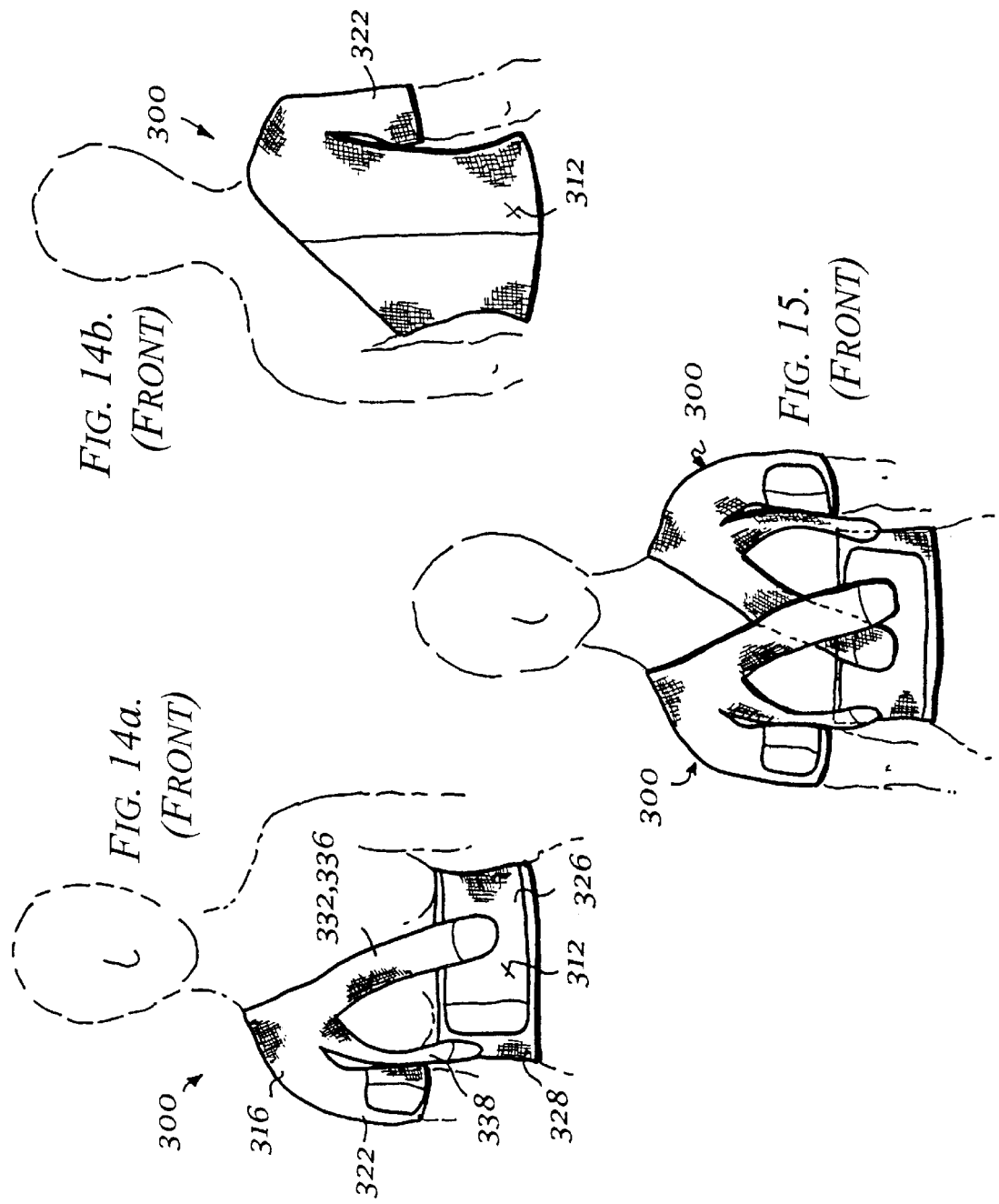

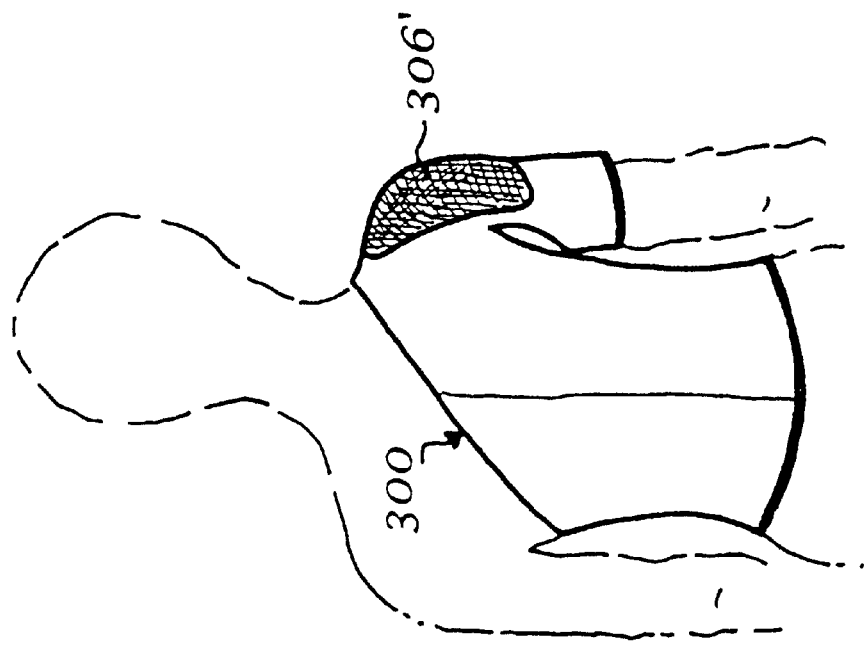
FIG. 16b. (REAR)
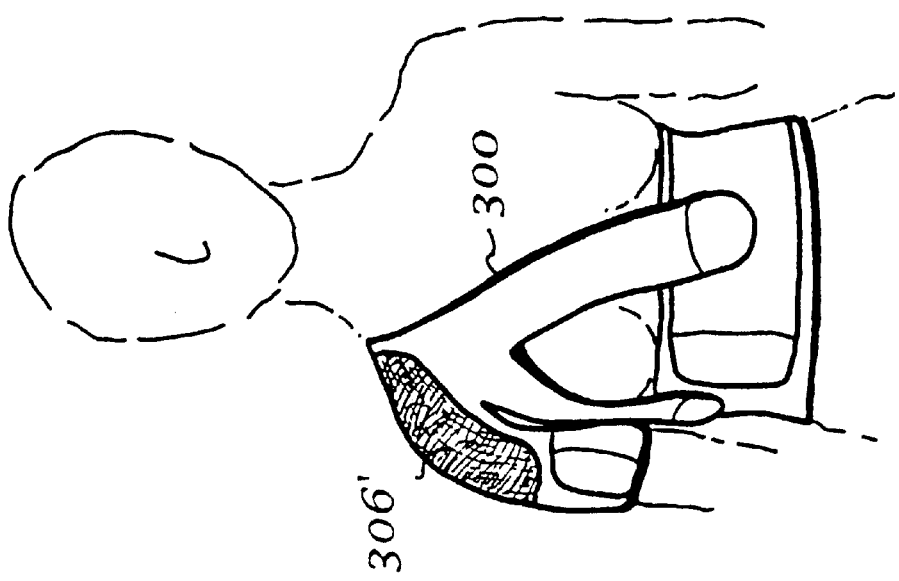
FIG. 16a. (FRONT)

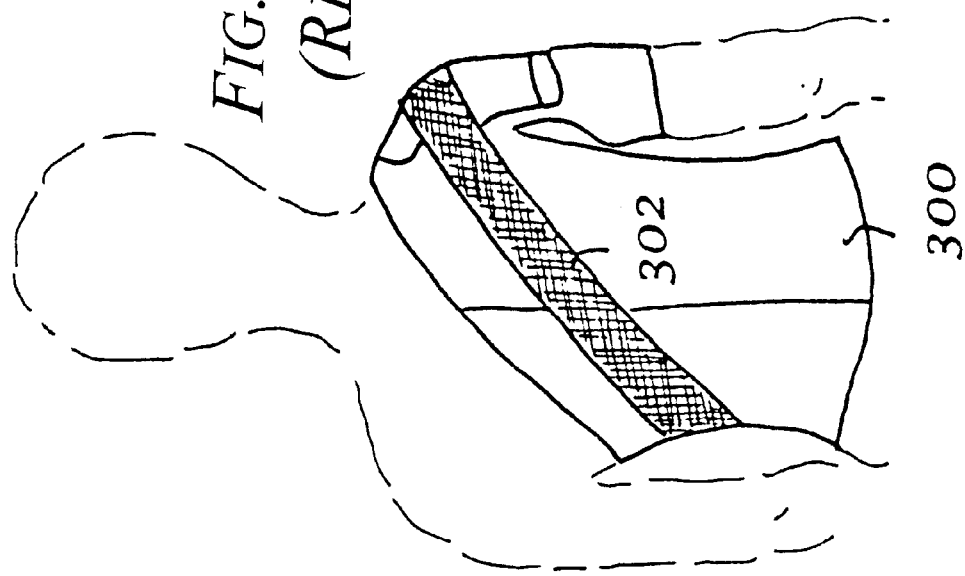
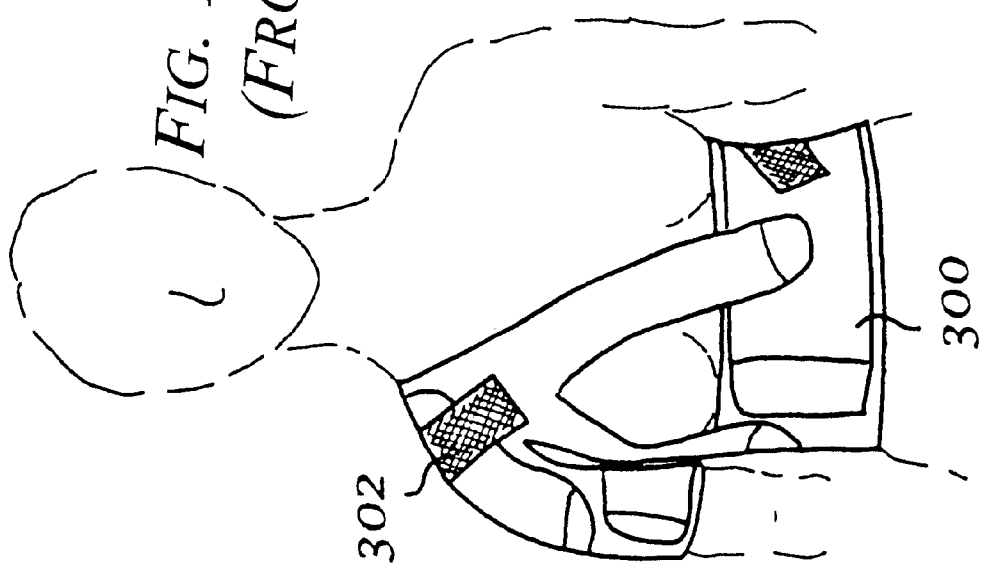

(FRONT)

(REAR)

ORTHOPEDIC GARMENT FOR DYNAMICALLY ENHANCING PROPER POSTURE

CROSS-REFERENCE TO PROVISIONAL APPLICATION(S)

This application claims the benefit of U.S. Provisional Application No. 60/168,115, filed Nov. 30, 1999.

BACKGROUND OF THE INVENTION

1. Field of the Invention

The invention relates to orthopedic braces, splints and bandages or the like, and, more particularly, to an elastomeric, orthopedic garment for disorders associated with the upper extremity, including the shoulder girdle. An orthopedic garment in accordance with the invention is provided for supporting and stabilizing the spine and/or one or more given articulations of the upper extremity that have a given disorder, malalignment and/or dysfunction, including without limitation dynamic scapular and acromio-clavicular stabilization, as well as dynamically enhancing proper posture. In other words, the given articulations include but are not limited to a group of joints or ligaments comprising the acromio-clavicular articulation, the coraco-clavicular ligaments, the shoulder joint, and the sterno-clavicular articulation. A central bone among this group of joints and ligaments is the shoulder blade bone, more properly called the "scapula."

2. Prior Art

As various terms of art are used in this written description, some more difficult than others, what follows is a brief overview of the pertinent anatomy, as presented and explained with general reference to FIGS. 1 through 5.

The bones that constitute the "upper extremity" of the human body consist of those of the shoulder girdle, the arm, the forearm and the hand. The shoulder girdle itself consists of two bones, the clavicle and scapula. FIG. 1 shows a rear view of a left scapula 20. The left scapula 20, as representative of a right scapula, is a large, generally flat or planar bone, triangular in shape, situated on the back of the rib cage (not shown) at an upper left border. The scapula 20 generally defines a plane; however, close examination reveals that the scapula 20 is slightly convex (from the rear view vantage point of FIG. 1). The scapula 20's rear surface is subdivided unequally by a spine 22 into two parts. The scapula 20 extends left to right in FIG. 1 between an internal or vertebral border and an external or axillary (i.e., arm pit) border. The spine 22 originates near the internal or vertebral border, and increases in mass as it extends to the external or axillary border, to where, at the margin of the external border, the spine 22 diverges from the plane of the scapula 20 and projects outward or beyond the external border to terminate in a prominence of bone mass, or a bone process formally called the acromion process 24.

The acromion process 24 is formed on its front surface with a concavity (not in view, but occurring at the position indicated by arrow 26) that forms an articulation with the outer extremity of the left clavicle 34 (not shown in FIG. 1, but see FIG. 2). The external or axillary border of the scapula 20 is formed with a cavity 36 called the glenoid cavity. The glenoid cavity 36 is spaced downwardly and slightly forwardly from the acromion process 24 and is the socket which forms the articulation with the humeral head 38 or "ball" (see FIG. 2) in the ball-and-socket joint of the shoulder. Above and in front of the glenoid cavity there is another prominence of bone mass or bone process, called the coracoid process 42.

FIG. 2 shows various articulations of the upper extremity, including the acromio-clavicular articulation 44, the coraco-clavicular ligaments 46, and the shoulder joint. The acromio-clavicular articulation 44 is formed between the outer extremity of the clavicle 34 and the front surface of the acromion process 24, and the ligaments of this articulation are collectively called the acromio-clavicular ligaments. The coraco-clavicular ligaments 46 serve to connect the clavicle 34 with the coracoid process 42 of the scapula 20.

The shoulder joint, as previously mentioned, is a ball-and-socket joint formed by the large globular head of the humerus 38, and the glenoid cavity 36 in the scapula 20, which receives the humeral head 38. The ligaments of the shoulder include a capsular ligament, a coraco-humeral ligament, a glenoid labrum (not shown), as well as the long tendon from the biceps. The capsular ligament generally encircles the ball-and-socket structure, and extends between the circumference of the glenoid cavity 36 in the scapula 20 and the anatomical neck of the humerus. The coraco-humeral ligament is a broad band which reinforces the upper part of the capsular ligament. The glenoid labrum (not shown) is a rim attached round the margin of the glenoid cavity. The long tendon of the biceps inserts as shown and becomes continuous with the glenoid labrum.

FIGS. 3, 4a and 4b show the muscles of the upper trunk, in which FIG. 3 shows the muscles of the upper back and FIGS. 4a and 4b the front of the chest.

With reference to FIG. 3, the muscles of the back are numerous and are for classification purposes subdivided in five layers, only the outer two of which are pertinent here. In the outermost layer is the trapezius muscle 48 which covers the upper back and part of the neck and shoulders. It has an elongated inner border that has an upper termination at the base of the skull and a lower termination down at the base of the dorsal vertebrae, and thus spans the length therebetween adjunct to all the cervical and dorsal vertebrae. From this inner border, the fibers of the trapezius muscle 48 converge as they extend outwardly, to converge on the inner margin of the scapula 20's spine 22 and acromion process 24. In the next layer are the rhomboid muscles 52, which extend in a flat band from an origin or inner border on the spinous process of generally the upper dorsal vertebrae, down and out to an outer extreme attached to the inner border of the scapula 20.

FIG. 4a shows that the muscles of the chest and shoulder area include the pectoral and the deltoid muscles 54, 56 and 58. The pectoralis major muscle 54 has a curved origin or inner border ranging from about the mid-point of the clavicle, and from there arcing in and down about as far as half-way down the sternum 60. The pectoralis major muscle 54 terminates in a flat tendon which is inserted into the humerus (see FIG. 2). The pectoralis minor muscle 56 (see FIG. 4b), which is covered by the pectoralis major muscle 54, terminates in a tendon attached to the coracoid process 42 of the scapula 20. The deltoid muscle 58, as shown by FIG. 4a, gives the rounded outline to the shoulder. Its name comes from its inverted-$\Delta$ shape. The deltoid muscle 58 has an extensive origin that arises from (i) the outer third of the clavicle 34, (ii) the acromion process 24 of the scapula 20, as well as from, (ii) the spine 22 of the scapula 20. From this extensive origin the fibers of the deltoid muscle 58 converge to form a tendon inserted in the shaft of the humerus.

FIG. 4b shows an inner layer of muscles of the chest, shoulder and arm area. The long tendon of the biceps attaches to the upper margin of the glenoid cavity 36 of the scapula 20. The short tendon attaches to the coracoid process 42. The serratus anterior (also serratus magnus) muscle 62 originates on the vertebral or inner border of the scapula 20 (refer to FIG. 1), and from there hugs the rib cage to extend to an opposite end where it terminates in a series of fingers attached to the ribs. The subacromial bursa 64 (along with the rotator cuff, discussed below) occupies the interspace between the humeral head 38 and the acromion process 24, and facilitates gliding therebetween. The subscapularis muscle 66 has a diverse origin, but it primarily originates in the subscapular fossa of the scapula 20 (see reference numeral 68 in FIG. 2). From its diverse origin, the subscapularis muscle 66 converges into a tendon attached to the front of the humeral head 38.

FIG. 5 shows the outer extremes of each of the supraspinatus muscle 70, the infraspinatus muscle 72, and the teres major and teres minor muscles 74 and 76. The outer extremes of each of these muscles attach to or around the humeral head 38. Three of these tendons, namely, the teres minor 76 and the supra- and infra-spinatus tendons 70 and 72, plus a fourth tendon, the subscapularis tendon 66 (see FIG. 4b), form what is more generally known in orthopedics and sports medicine as the rotator cuff.

The shoulder joint is capable of movement in every direction, namely, forwards (flexion) and backwards (extension), out and up from the side (abduction), and into the side (adduction), as well as rotation (spinning) inwards (internal rotation) and outwards (external rotation), plus circumduction (pivoting). The scapula 20 is capable of being moved upwards (elevation) and downwards (depression), forwards (protraction) and backwards (retraction), as well as circumduction (pivoting) from a given resting alignment out and up (lateral or upward rotation), or in and down (medial or downward rotation), over the back of the rib cage. The muscles which raise the scapula 20 include the upper fibers of the trapezius 48 and the two rhomboids 52; those which depress it include the lower fibers of the trapezius 48 and the pectoralis minor 56. The scapula 20 is drawn backwards by the rhomboids 52 and the middle and lower fibers of the trapezius 48, and forwards by the serratus anterior 62 and pectoralis minor 56, assisted by, when the arm is fixed, the pectoralis major 54. The literature indicates the average range for scapular elevation and depression is between 10 and 12 cm, the average amount of protraction and retraction is 15 cm, and the average range of circumduction (pivoting) is between opposite extremes about 60° apart. See, e.g., K. Andeway, "Scapular Malalignient in Upper Quadrant Dysfunction," in PT Magazine, July 1994, pp. 60–65.

There are various disorders or pathologies to the areas of the neck, the shoulder, the upper trunk as well as the temporo-mandibular joint (i.e., the jaw), the treatment of which can involve proper dynamic positioning of the posture and/or dynamic stabilization of the scapula, as will be more fully explained below. What is needed is an effective orthopedic garment for properly, dynamically positioning the posture and/or dynamically stabilizing the scapula, which garment can be dressed into by a patient, male or female, without outside or professional help (following, of course, an original fitting and course of instruction in the use of the garment), and which is multiply adjustable for comfort and/or special support, wearable under regular clothing, re-usable, economical, and non-allergenic to the skin of the patient.

SUMMARY OF THE INVENTION

Various objects and aspects in accordance with the invention are provided by an orthopedic method comprising utilization of a base garment and a halter strap system for dynamically enhancing proper posture.

The base garment is elastic and comprises left and right shoulder-draping portions, a waist band, and intermediary material for extending between and operatively interconnecting the shoulder-draping areas and the waist band. The intermediary material be produced in the format of one or more straps or bands. Alternatively, the base garment can be produced in the format of a tube such that the base garment resembles a camisole or, that is, a sleeveless and collarless body stocking. Sleeves and collars are optional but as they do not materially contribute to the functions of the base garment, they are preferably omitted for the patient's comfort.

The waist band and shoulder pads preferably are provided with diverse inner and outer surfaces. The inner surface is preferably adapted for high friction contact with the patient's skin or a thin undergarment worn by the patient. The outer surface is preferably provided with hook-fastener securing areas.

An inventive aspect relates to a pair of elastic halters, which have hook-fastener tag ends. The halter's hook-fastener tag ends are secured to the base garment's hook-fastener securing areas to achieve the following. That is, the halters cross each other diagonally across the patient's back. That way, one halter supplies tension between an origin on the front of the right shoulder-draping portion and a termination on the waist band over the abdomen, by a course arching behind the right shoulder then diagonally across the back and around the patient's left side. Concurrently, the other halter supplies tension between an origin on the front of the left shoulder-draping portion and another termination on the waist band over the abdomen, by a course arching behind the left shoulder then diagonally across the back and around the patient's right side. Accordingly, the halters provide diagonally-crossing filaments of tension across the patient's back in order to oppose slouching and thereby enhance proper erect posture.

Another inventive aspect relates to a means for stationing the intersection where the halters cross in the back to a preferred given station. Given that the intermediary material preferably includes a dorsal span, the halter-stationing means is located on the dorsal span at about such intersection where the halters cross in the back. The halter-stationing means affords maintenance of the courses the halters utilize to extend and retract in, despite the patient's twisting, bending and other bodily contortions. It's not so much that the patients are performing acrobatics. But rather, even if the patient's have diminished posture function, they are not going to sit, stand or walk without ever flexing or twisting the back. It is an object of the invention to provide posture support for the patient even when the patient is in motion, and not just when at rest or certainly not merely when plainly immobilized.

The halter-stationing means can take the format of diagonally-crossing casements attached to the dorsal span. With casements, preferably the halter tag ends are enlarged to make it difficult to inadvertently retract the halter ends in through any casement slit (eg., entrance or exit). Or, among other possible alternatives, the halter-stationing means may take the format of fasteners—such as Velcro™ fasteners, stitches or even adhesive—for fastening the intersection of the crossing halters to the given station on the dorsal span.

In one version of the base garment, the shoulder-draping portion comprise shoulder pads as the intermediary material comprises a stocking-like tube spanning between the waist band and shoulder pads. The stocking material preferably is elastic and has an inner surface adapted for high friction contact with the patient's skin or a thin undergarment worn by the patient.

Optionally, the waist band would include overlapping belt ends, one of which belt ends is provided with hook fasteners to allow releasable tightening or slackening of the waist band around the patient's waist. That way, the waist band can be slackened for sitting or cinched tighter when standing and so on. In other words, the waist band can be adjusted for comfort. In cases where the belt-end version of the waist band is joined with the stocking-version of the intermediary material, preferably the stocking portion is slit above where the belt ends overlap to accommodate pleating.

The foregoing orthopedic method might further include the following enhancement. That is, there might be provided an elastic tension-relieving sleevelet for securing to the base garment. Such a sleevelet would include an upper-arm encircling portion for securing to the patient's upper arm. It would also include one or more spaced attachment points featuring with hook fasteners in order to allow fastening to one or the other shoulder-draping portions of the base garment. Wherein, the tension-relieving sleevelet provides relief to the tension in the muscles and nerves connected to and responsible for moving the scapula as well as obviates compensation from accessory muscles such as ones that move the upper arm. It will be recognized that the tension-relieving sleevelet substantially overlies the deltoid muscle.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 3 is a rear perspective view of muscles of the back, wherein, on the left side is exposed the most exterior layer of muscles, and, on the right side, a first interior layer and parts of a second;

FIG. 5 is a rear perspective view of muscles of the shoulder and arm, the right side being broken away;

FIG. 8a is a front perspective view comparable to FIG. 7 except showing attachment of a trapezius strap to the base;

FIG. 8b is a rear perspective view thereof;

FIGS. 9a through 9d are a series of front perspective views that illustrate a given classification scheme of injuries to the acromio-clavicular articulation, wherein:

FIG. 9a shows a normal acromio-clavicular articulation,

FIG. 9b shows an acromio-clavicular articulation with sprained acromio-clavicular ligaments, and is classified a TYPE I injury, FIG. 9c shows an acromio-clavicular articulation with disrupted acromio-clavicular ligaments and sprained coraco-clavicular ligaments, and is classified a TYPE II injury, and, FIG. 9d shows an acromio-clavicular articulation with disrupted acromio-clavicular and coraco-clavicular ligaments, and is classified a TYPE III injury;

FIG. 11a is a front perspective view of the FIG. 10 orthopedic garment as worn by a patient, whose outline is shown dashed lines, wherein an auxiliary strap is shown with one end attached to the right shoulder of the garment on the patient;

FIG. 11b is a front perspective view comparable to FIG. 11a except showing the auxiliary strap with its opposite end attached to the garment under the left breast of the patient;

FIG. 11c is a front perspective view comparable to FIG. 11b except showing the completed attachment of a second auxiliary strap in mirror opposite relation to the first strap;

FIG. 12a is a rear perspective view of FIG. 11a;

FIG. 13 is a front perspective view of still another embodiment of the orthopedic garment in accordance with the invention, for dynamic scapular stabilization and the like;

FIG. 14a is a front perspective view thereof as worn by a patient, whose outline is shown in dashed lines;

FIG. 14b is a rear perspective view thereof;

FIG. 15 is a front perspective view of opposite left and right versions of the base garment of FIG. 13 shown worn by one patient at the same time in order to obtain the equivalence of a bilateral garment;

FIG. 16a is a front perspective view comparable to FIG. 14a except showing attachment of a deltoid strap to the base;

FIG. 16b is a rear perspective view thereof;

FIG. 17a is a front perspective view comparable to FIG. 14a except showing attachment of a trapezius strap to the base;

FIG. 17b is a rear perspective view thereof;

DETAILED DESCRIPTION OF THE INVENTION

Figure 6:
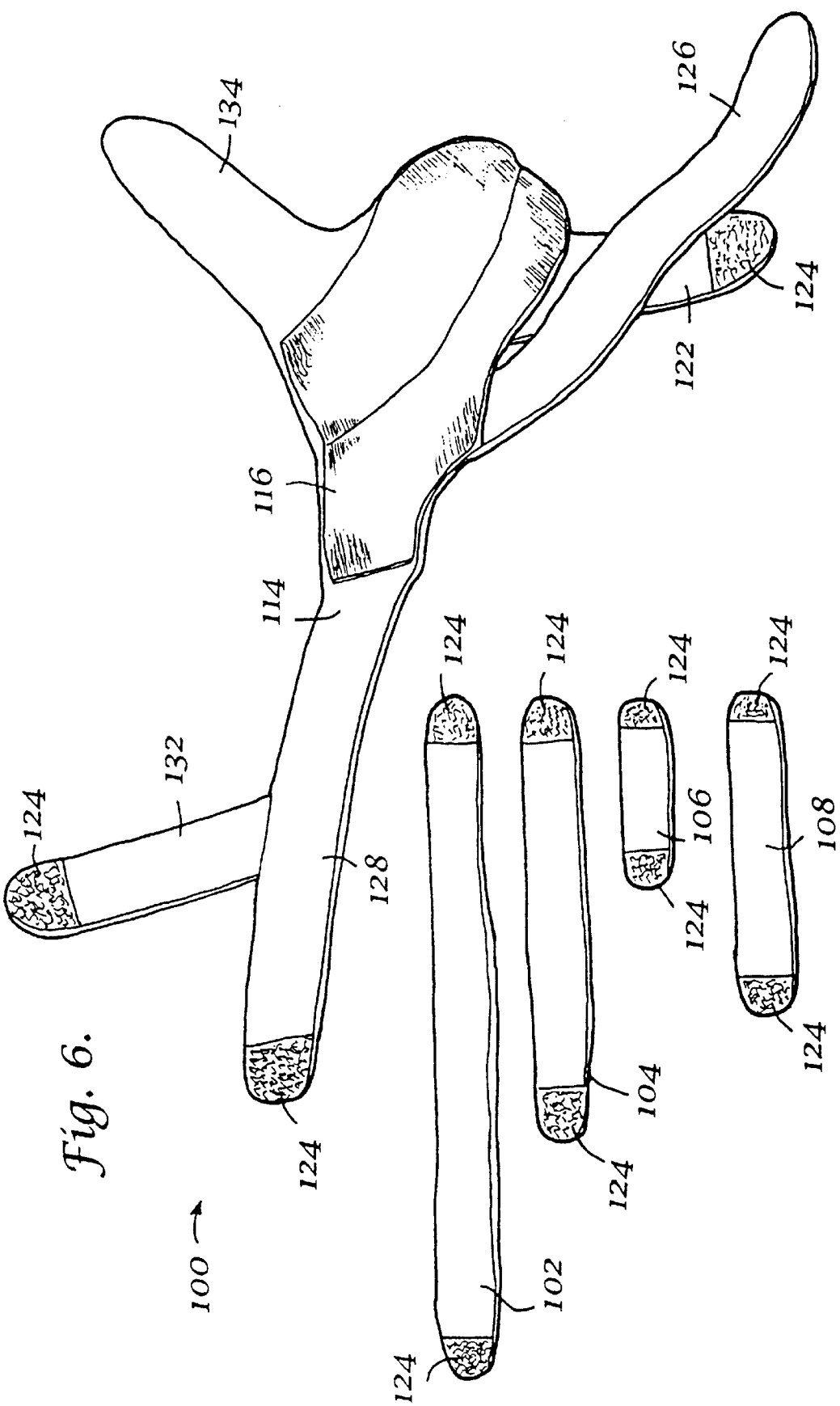
FIG. 6 is a perspective view of an orthopedic garment in accordance with the invention for dynamic scapular stabilization.

In FIG. 6, an orthopedic garment 100 in accordance with the invention is stretched out as generally resting flat on a given horizontal surface (not shown). Along with the garment 100, there is shown at least on auxiliary strap 102 for enhancing the effectiveness of the garment 100. The orthopedic garment 100 has an outer surface 112 (see FIG. 7) and an inner surface 114 opposite to the outer surface 112. As shown by FIG. 6, the orthopedic garment 100 is resting with its outer surface 112 down and its inner surface 114 up.

Figure 7:
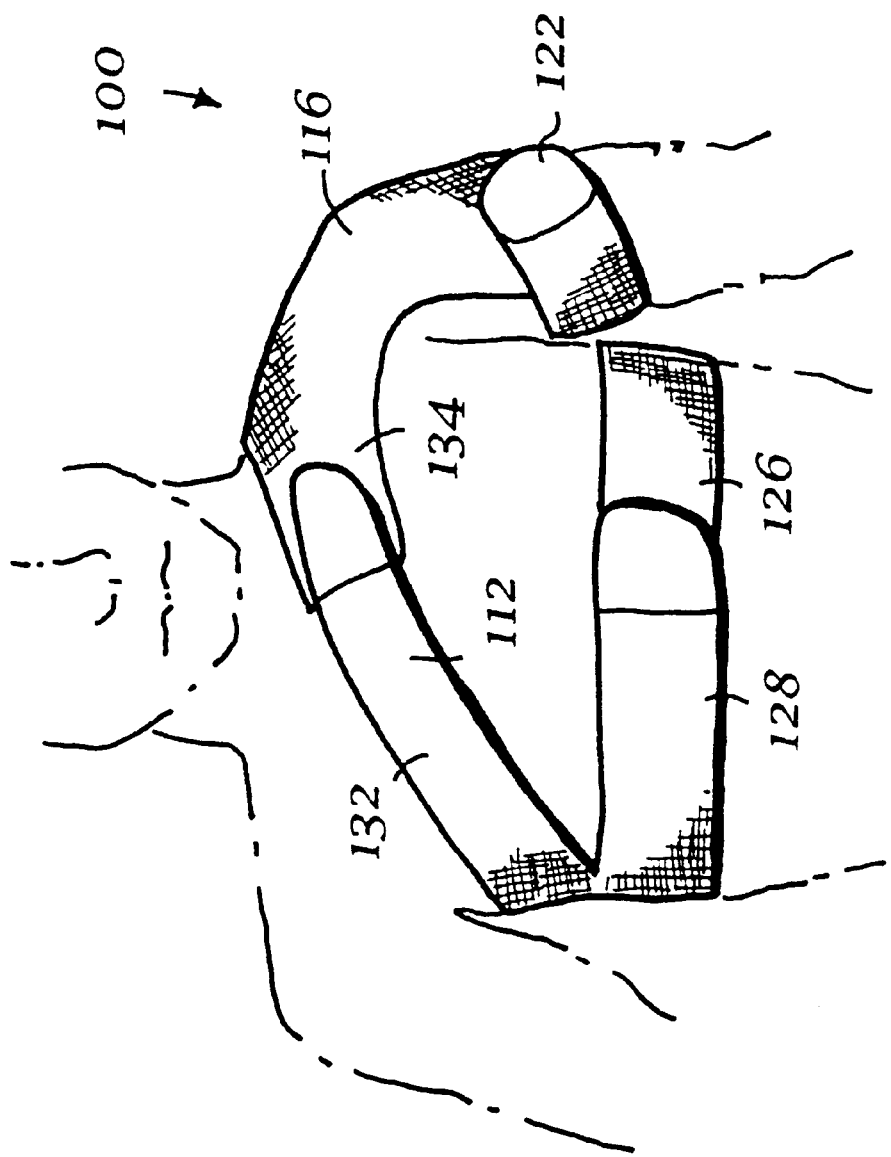
FIG. 7 is a front perspective view thereof as worn by a patient, whose outline is shown in dashed lines.

The material used in the orthopedic garment 100 includes a neoprene or like resilient material that forms a core which is covered by an inner liner that defines inner surface 114 (i.e., inner relative to the inner surface) and an outer liner that defines outer surface 112 (see FIG. 7). The inner liner which defines inner surface 114 can be Terry™ cloth or a like material which is comfortable to the skin yet absorbs perspiration, allows the skin to ventilate, and thereby minimizes trapping dampness against the skin. The outer liner which defines outer surface 112 (FIG. 7) is made of a nylon weave or the like that is Velcro™ compatible, i.e., it forms a pile for closure with hook material of a hook-and-pile fastening system (e.g., Velcro™).

Parts of the inner liner (which defines inner surface 114) are covered by chamois or a like material in the portions 116 of the garment that rest against the outer arm and the top of shoulder, including the scapula. The chamois 116 or the like is chosen for its ability to frictionally grab the skin of the patient and minimize or eliminate slipping therebetween, but also be comfortable and non-allergenic to the skin of the patient.

The orthopedic garment 100 shown by FIG. 6 is arranged and configured for treating pathologies of the left shoulder. It could be alternatively arranged in a mirror opposite version for a right shoulder. It also could be arranged for bilateral treatment of the left and right shoulders concurrently. Accordingly, terms like "left" and "right" are used merely for convenience in this description and do not limit the invention to the particular arrangement shown in the drawings.

The shape and arrangement of the orthopedic garment 100 includes the arm and shoulder portion 116 which, as mentioned above, is covered on the inner surface with chamois or a like non-slip material for frictionally grabbing the skin of the patient. The garment also includes an arm strap 122 which terminates in a patch 124 of hook material for closure with the outer liner (which defines outer surface 112) of the arm and shoulder portion 116 in order to form a sleeve, as shown by FIG. 7. The garment 100 further includes a pair of generally opposite chest straps 126 and 128 extending from a generally common root in the arm and shoulder portion 116, to extend in opposite directions therefrom and meet each other in the front of the chest of the patient (see FIG. 7) as a belt worn around the chest under or below the breasts. The right (i.e., the patient's or wearer's right) chest strap 128 includes a fork 132 which, when the right chest strap 128 is wrapped around the patient, diverges from the right chest strap 128 approximately under the right or non-involved arm pit of the patient. The fork strap 132 extends therefrom diagonally upwards above the breast and across the front of the chest of the patient to meet a down flap 134 that extends diagonally down to the fork strap 132 from the arm and shoulder portion 116 of the garment, as shown by FIG. 7. FIG. 6 also shows the arrangement and location of various patches 124 of hook material on the garment 100's inner surface 114.

In use, the orthopedic garment 100 is worn by the patient as shown by FIG. 7. The arm strap 122 forms a loop with the arm and shoulder portion 116 to define a sleeve, and is worn on the involved arm (i.e., the left arm here, or whichever side of the patient that has the given pathology). The opposite chest straps 126 and 128 form a loop or belt around the chest of the patient and fasten together approximately in the middle of the front of the chest below the breasts. The fork strap 132 extends diagonally up to the down flap 134 of the arm and shoulder portion 116, and the fork strap 132 and down flap 134 likewise fasten together approximately in the middle of the front of the chest above the breasts. It is an inventive aspect of the garment 100 that the various straps diverge above or below the breasts of the patient so that the garment is as comfortable for use by female or heavy-breasted patients (male or female) as well as by flat-chested patients.

Another inventive aspect of the orthopedic garment 100 relates to its configuration and arrangement so that the patient can preferably dress into the orthopedic garment 100 alone, by him or herself without professional or outside help, even with an immobile left arm. The steps that the patient should take to do this are preferably the following.

First, the patient should form the sleeve via the arm strap 122 and the arm and shoulder portion 116. If the patient is not too immobile, he or she might be capable of doing this directly on his or her arm. Alternatively, if the patient is too stiff or immobile to do that, the patient could build the sleeve before-hand, and then slip his or her left arm into the pre-built sleeve. By whichever way the patient gets his or her arm into the sleeve, the patient follows that with forming the chest loop or belt via the opposite chest straps 126 and 128. Finally, the patient should secure the fork strap 132 with the down flap 134. These last two steps require an act of fastening that occurs in the front of the chest of the patient, which can be accomplished even by a patient with an immobile left arm.

FIGS. 8a and 8b though 11b show the attachment and arrangement of the auxiliary strap 102. The material used to make the strap is neoprene or a like resilient material, with hook patches 124 affixed at the opposite ends thereof (see FIG. 6). The strap 102 is approximately 28 inches (70 cm) long.

In FIGS. 8a and 8b, this strap 102 is referred to as a trapezius strap because clinical evidence suggests that it enhances the positioning of and pull on the scapula ordinarily achieved by the middle and lower fibers of a healthy trapezius muscle 48 (see, e.g., FIG. 3). The trapezius strap 102, like the orthopedic garment 100 generally and like the other two straps 104 and 106 as well, preferably can be affixed and adjusted to comfort by the patient alone, without outside help. To do this, the patient attaches one end of the strap 102 to the outer liner (which defines outer surface 112) of the orthopedic garment 100 on the front of the shoulder as shown in FIG. 8a. In fact, the preferred location is approximately on the front of the acromion process of the scapula. From this origin, the trapezius strap 102 is looped behind the back of the patient and under the uninvolved arm pit to be secured to the chest strap(s) 126/128 of the orthopedic garment as shown in FIG. 8a. FIG. 8b shows how the trapezius strap 102 is arranged across the back. The end of the trapezius strap 102 that attaches to the chest strap(s) 126/128 is tightened or loosened as desired by trial and error until a comfortable or supportive fit is achieved.

Given the foregoing, the orthopedic garment 100 in accordance with the invention is useful for dynamic scapular stabilization by improving the biomechanics of the scapula, and hence the whole shoulder girdle, by promoting proper scapular positioning and movement mechanics as the scapula is moved through its motions. Other advantages include the following. The garment 100 naturally enough promotes the proper resting alignment of the scapula. It enhances proper positioning and gliding of the humeral head (ball) in the scapula's glenoid cavity (socket). It gives additional support to the muscles connected to and responsible for moving the scapula, and thereby (i) relieves tension in those muscles as well as (ii) obviates compensation from accessory muscles and thus prevents secondary pathologies or muscle strains as resultant from the base or primary pathology.

A given patient has a need for dynamic scapular stabilization when he or she suffers from a diverse variety of shoulder, neck and arm pathologies, including without limitation the following kinds:—namely, (i) acromio-clavicular strains, (ii) various impingement syndromes, (iii) thoracic outlet syndromes, and, (iv) the "winged" scapula condition.

Acromio-clavicular strains and separations are shown in FIGS. 9a through 9d. FIG. 9a shows a normal joint. FIG. 9b shows an injury that resulted from a mild force to the point of the shoulder, which produced a minor strain to the fibers of the acromio-clavicular ligaments 44. This injury is a TYPE I injury. The acromio-clavicular ligaments 44 remain intact, and the acromio-clavicular joint remains stable. FIG. 9c shows a TYPE II injury. A moderate force to the point of the shoulder is severe enough to rupture the acromio-clavicular ligaments 44. The outer extremity of the clavicle 34 is unstable because the scapula 20 is attached to the clavicle 34 only by the coraco-clavicular ligament 46. The scapula 20 may adversely rotate inwardly (counterclockwise in FIG. 9c) and thereby widen the acromio-clavicular joint 44. The scapula 20 might also shift slightly downwards relative to the outer extremity of the clavicle 34. There may be minor stretching to the coraco-clavicular ligament 46.

FIG. 9d shows a TYPE III injury. A severe force to the point of the shoulder has disrupted the acromio-clavicular and coraco-clavicular ligaments 44 and 46. The distal end of the clavicle 34 appears to have sprung up as a sprung piano key or the like. Appearances aside, the actual deformity is truly the downward displacement of the scapula 20 and entire upper extremity relative to the generally stationary clavicle 34. The deltoid and trapezius (not shown) are likely disrupted from the outer extremity of the clavicle 34 also.

Figure 2:
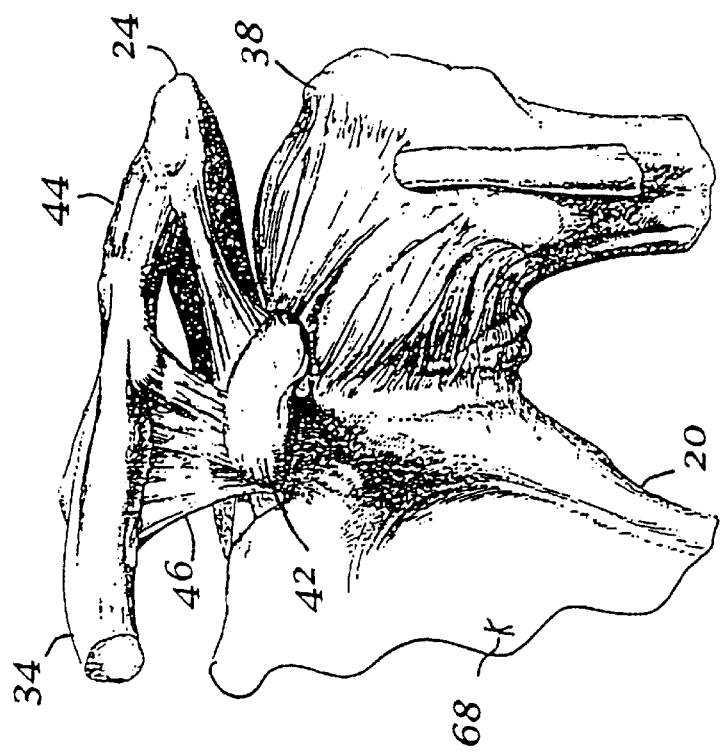
FIG. 2 is a front perspective view of the upper extremity of the human body, with the right side and portions of the left arm being broken away.
Figure 1:
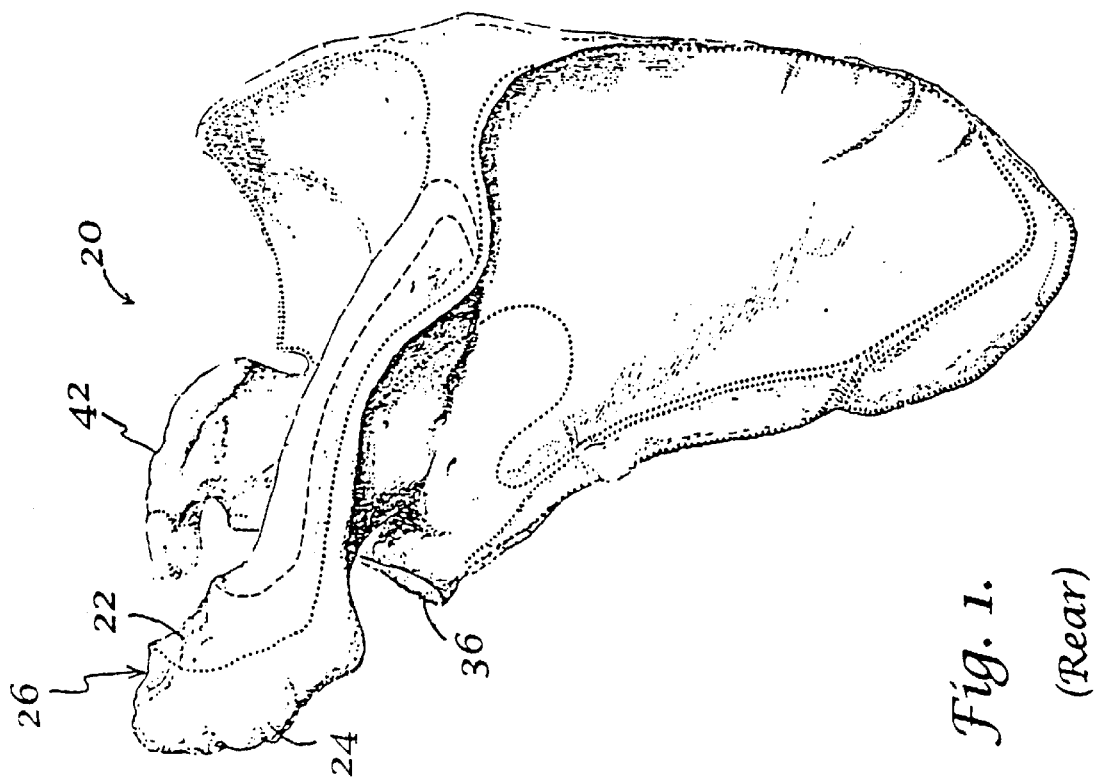
FIG. 1 is a rear perspective view of a left-side human shoulder blade:—i.e., scapula bone.
Figure 4B:
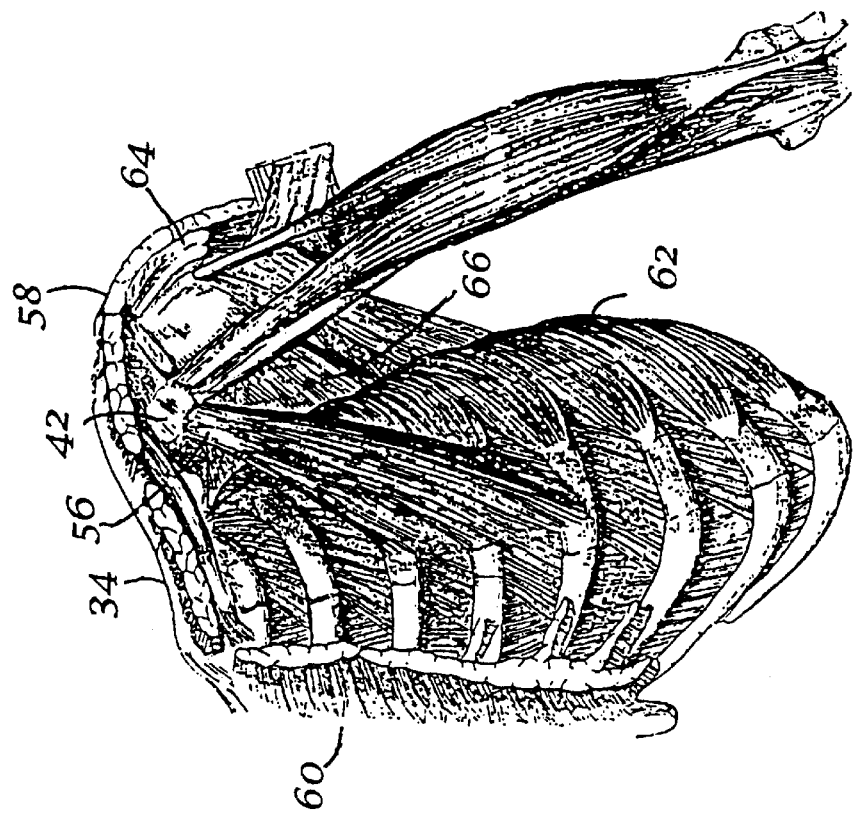
FIG. 4b is a front perspective view of interior muscles of the chest and shoulder, the right side being broken away.
Figure 4A:
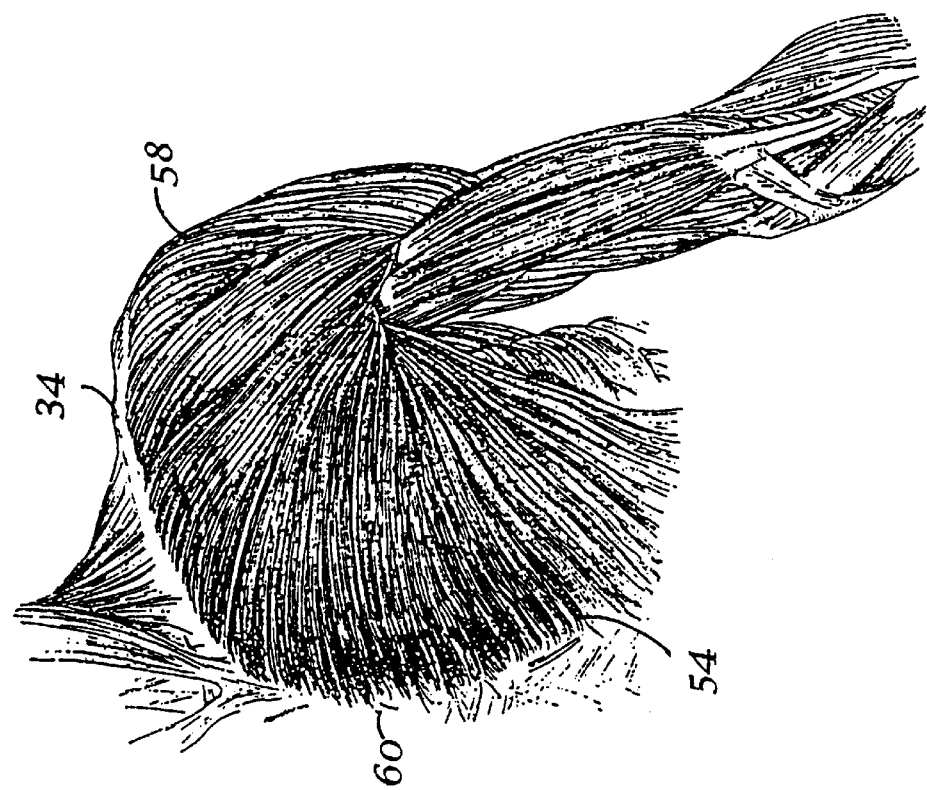
FIG. 4a is a front perspective view of the most exterior layer muscles of the chest and shoulder, the right side being broken away.

Impingement syndrome injuries commonly occur in, but by no means limited to, athletes. Impingement syndrome injuries in the shoulder and arm area include, rotator cuff tendinitis, and, subacromial bursitis. With reference to FIG. 4b, subacromial bursitis is inflammation of the bursal sac and membrane 64 positioned directly below the acromion process 24 of the scapula 20 (compare, e.g., FIG. 2). A typical cause of this inflammation is due to the abnormal constriction of the interspace between the acromion process 24 and the humeral head 38. When that happens, the subacromial bursa 64 can become "pinched" or compressed, and sorely inflame as a result.

To turn to FIGS. 4b and 5, rotator cuff tendinitis involves inflammation of any of the four tendons that constitute the rotator cuff, which are, as previously stated, the teres minor tendon 76, the supra- and infra-spinatus tendons 70 and 72, and the subscapularis tendon 66. Sports medicine data shows that rotator cuff injuries most commonly involve pinching of or inflammation in the supra- and infra-spinatus tendons 70 and 72, less commonly so in the subscapularis tendon 66, and only rarely in the teres minor tendon 76.

The thoracic outlet syndrome can be caused by, among other things, a drooping shoulder girdle. The nerve bundles that extend into the arm, as well as the artery and vein that supply and vent the arm, pass closely underneath the clavicle en route across the arm pit to the arm. Thoracic outlet syndrome is characterized by compression of these nerve bundles and/or arterial vessel, say, in the clavicular area, which manifests as pain in the arms, prickling in the fingers, weakness and wasting of the small muscles in the hand, and so on. In cases of thoracic outlet syndrome, it is not just generally the arterial system which is involved but, more often, the thoracic outlet syndrome is a condition of the venous system. Such compression, needless to say, is caused by improper alignment or positioning of an abutting or adjacent structure to the compressed nerve bundles or arteries. If this occurs in an improperly drooping shoulder girdle, which in any given case it may, then the orthopedic garment in accordance with the invention (as will be more particularly described below) is effective in supporting and dynamically stabilizing the shoulder girdle for proper positioning and biomechanics.

The "winged" scapula condition may be a special case of the thoracic outlet syndrome, or trauma or disease. Here, a nerve, called the long thoracic nerve, can be compressed, injured, or compromised, which results in partial or complete paralysis of the serratus anterior, and hence further results in the scapula sticking out and giving the appearance of a "wing." The orthopedic garment in accordance with the invention is effective in restoring proper alignment in a winged scapula.

The orthopedic garment in accordance with the invention can also be utilized in conduction with a generic arm sling/support when more aggressive support or unloading is desired in conjunction with the benefits of scapular control support as already described. For example, neurological insults such as cerebral vascular accident (CVA) or stroke, or more severe Grade III AC separations.

Among the above-described disorders, generally speaking, the longer or more chronic thee condition/disorder/dysfunction, the longer and more difficult it is to properly rehabilitate. It is the clavicular-type of trauma (e.g., motor vehicle accident with the shoulder harness portion of the seat belt) involving any or all of the acromio-clavicular, coraco-clavicular, and/or the stemo-clavicular joints/ligaments, that characteristically results in significant soft tissue trauma throughout the shoulder girdle. The clavicular-type of trauma is frequently accompanied by or associated with neck injuries too, and so can develop into thoracic outlet symptoms, which are the most enduring and require relatively long-lasting treatment programs.

The orthopedic garment in accordance with the invention is a highly practical adjunctive measure for treating the already described disorders of the shoulder girdle, whether of a fairly recent onset or whether of a more chronic condition. As a result, the patient's symptoms are more easily managed not only in the clinic but also at home throughout the day, thereby facilitating improved function and independence. With symptoms more manageable, and proper biomechanics restored or enhanced, the professional physical rehabilitation specialist—physical therapist—now has an improved opportunity to more effectively rehabilitate the shoulder girdle through a method of proper training of the involved muscle groups in conjunction with the inventive orthopedic garment, and eventually eliminate the need for further use of the inventive orthopedic garment.

In addition, the cost in material and professional time of frequently-applied adhesive tape wraps and the like is eliminated since the patient is able to dress him or herself into and out of the garment without outside help. The inventive orthopedic garment is comfortable to the skin and thus can be worn for indefinitely long periods of time discreetly under normal clothing without irritating or raising a rash in the skin, which frequently occurs with taping and the like. In view of the foregoing, the inventive orthopedic garment is highly economical.

The inventive orthopedic garment also enhances smooth and coordinated motor control apparently by virtue that it closely surrounds and compresses comfortably against the skin and muscle of the patient. In more difficult language, the inventive orthopedic garment gives the patient appropriate, tactile, proprioceptive input. To understand this better involves a brief explanation of the motor control functions of the nervous system.

In the performance of smooth and coordinated motor tasks—whereas there is no doubt that the signals sent to the muscles which energize movement are important—there is an important unconscious "feedback" signal which is sent from the muscles, which feedback signal conveys information regarding the position and movement of the muscles and joints. The nerves that are embedded in the muscles, the tendons and the joint capsules, which give these signals, are called proprioceptors. These feedback signals from the proprioceptors are known to be important to smooth and coordinated muscle control.

When there is injury or inflammation to the tissue surrounding a given proprioceptor, it disturbs proper signal generation by the proprioceptor and, as a result, faulty mechanics in muscle control occur. It has been found that by wearing the inventive orthopedic garment, a patient improves and/or restores smooth and coordinated muscle control. This result is attributed to several factors, but among those factors, it is partly attributed to the inventive orthopedic garment providing appropriate tactile proprioceptive input. Put differently, the compression or support (i.e., tactile input) that the garment 100 gives to the offended tissue appears to stimulate or enhance more proper proprioceptive signal generation. With a proper feedback signal apparently restored, smooth and coordinated motor control returns.

Figure 10:
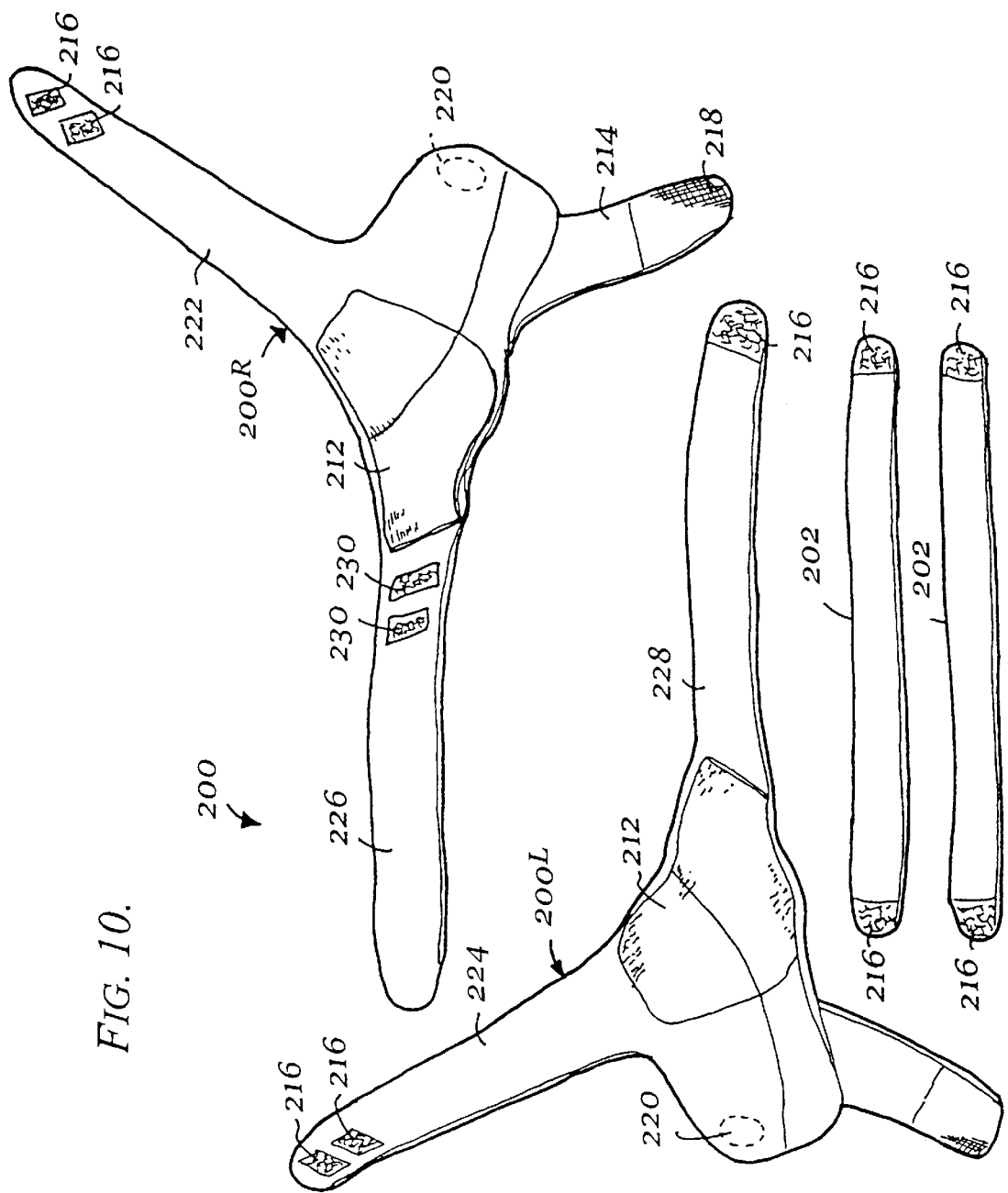
FIG. 10 is a perspective view of an alternate orthopedic garment in accordance with the invention for dynamically enhancing proper posture in the upper extremity.

FIG. 10 shows an alternate orthopedic garment base 200 in accordance with the invention for dynamically enhancing proper posture in the upper extremity. The orthopedic garment 200 includes left and right base portions $200^L$ and $200^R$ shown resting flat on a given horizontal surface (not shown), and beside the base portions $200^L$ and $200^R$ are a pair auxiliary straps 202. The base portions and straps $200^L$, $200^R$ and 202 have respective outer surfaces (see FIG. 11a) and inner surfaces opposite the outer surfaces. In FIG. 10, the outer surfaces are down and the inner surfaces are up. The FIG. 10 base portions and straps $200^L$, $200^R$ and 202 are made from comparable materials as previously described above in connection with the FIG. 6 garment and straps 100 and 102. Thus the FIG. 10 base portions and straps $200^L$, $200^R$ and 202 comparably include arm and shoulder portions 212 made of chamois or a suitable substitute (as explained previously), as well as patches of hook and pile material 216 and 218. The hook and pile patches 216 and 218, however, insofar as the base portions $200^L$ and $200^R$ are concerned, are arranged differently relative to the FIG. 6 garment 100, as will be explained next. These differences could be incorporated in the FIG. 6 garment 100 if desired to give the FIG. 6 garment 100 the same advantages.

The left base portion $200^L$ is worn by the patient over his or her left shoulder (see FIG. 11a), and appears on the right side of the view of FIG. 10. Each of the left and right base portions $200^L$ and 200 has an arm strap 214. Each arm strap 214 has a patch of pile material 218 on the inner side thereof, which distinguishes the FIG. 10 arm straps 214 with the FIG. 6 arm strap 122. In FIG. 6, the arm strap 122 has a patch of hook material sewn to the inner side. For the FIG. 10 arm straps 214, the corresponding patches of hook material 220 are on the outside of the liner, and are shown in dashed lines. Either way (i.e., either FIG. 6 or 10), the arm straps 214 (or 122) are adjustable for forming sleeves to wear around a patient's arm above the elbow. However, placing the hook patch 220 on the outside of the garment 200, as shown by FIG. 10, keeps the hook material oriented away from the patient's skin. It is desirable if the hook patch 220 does not rest against the patient's skin while the left or right base portions $200^L$ or $200^R$ are worn because the hook material is known to irritate the skin.

The left and right base portions $200^L$ and $200^R$ have front straps 222 and 224, respectively, that extend diagonally across the front of the patient (i.e., across his or her chest) just above his or her breast (see FIG. 11a). As shown by FIG. 11a, either one of the front straps 222 or 224 does about the same work as three straps in the FIG. 6 garment 100: namely, the two opposing chest straps 126 and 128 as well as the fork strap 132. In comparison, the left front strap 222 (see FIG. 11a) is one piece relative to the opposing chest straps 126 and 128 (see FIG. 7) being two pieces, and the fork strap (FIG. 7) is omitted from the left front strap 222 (FIG. 11a).

Figure 12A:
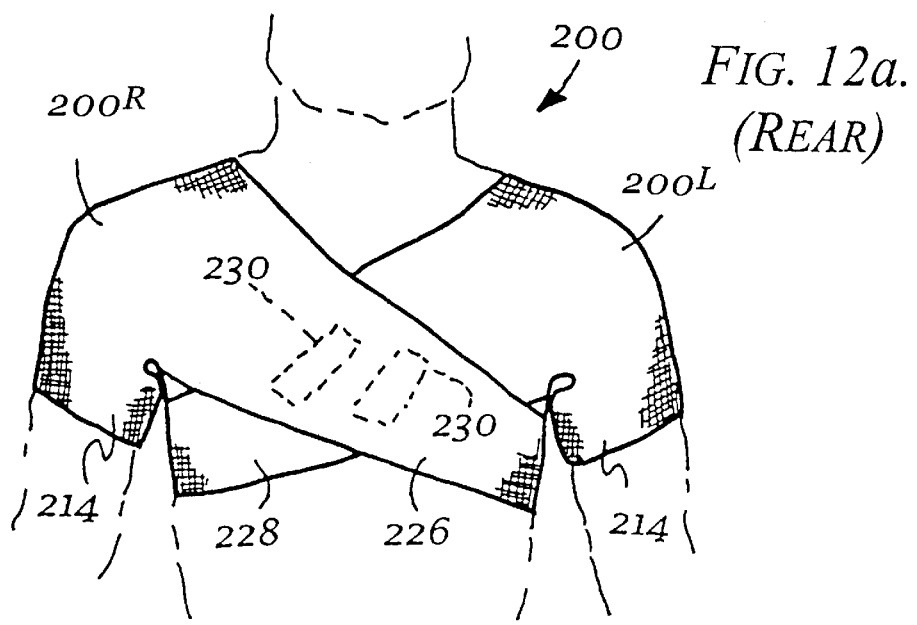

The left and right base portions $200^L$ and $200^R$ also have back straps 226 and 228, respectively, that extend diagonally across the patient's back (see FIG. 12a), which back straps 226 and 228 further extend under the opposite side arm pit (i.e., as again shown by FIG. 12a). FIG. 11a shows that the terminal end of the left side back strap 226 comes from underneath the patient's right arm pit to fasten together with the back strap 228 of the right base portion $200^R$. FIG. 11a also shows that the back strap 228 of the right base portion $200^R$ is looped around underneath the patient's left arm pit. The oppositely extending back straps 226 and 228 fasten together in front in the middle of the patient's chest for ease of convenience for the patient to attach by him or herself, without help from another person.

FIG. 10 shows that the back strap 228 of the right base portion $200^R$ has a patch of hook material 216 near its terminal end, whereas the back strap 226 of the left base portion $200^L$ does not. Only one of the two back straps 226 or 228 needs a patch of hook material, it being omitted from the other back strap 228 or 226 as redundant and needless.

FIG. 10 also shows that the front straps 222 and 224 have two patches 216 of hook material near their respective terminal ends. These two patches 216 allow adjustment for the size of the patient, whether if the patient has a relatively larger or smaller torso than another patient (these differences not shown). In use, the patient would determine which front strap hook patch he or she would use—based on trial and error—for comfort. After having made that determination, the patient would then cover the unused hook patch with a patch of pile material (not shown), which would rest against the patient's skin so that the patient would feel soft material as, for example, the inner liner of the base portions $200^L$ or $200^R$. That way, the unused hook patch 216 on the front strap 222 or 224 would be covered from irritating the patient's skin.

The left base portion 200L has affixed to the back strap 226 a pair of strips 230 of hook material, as near the arm and shoulder portion 212 as shown by FIG. 10. The use of these hook strips 230 is for fastening to the outer liner of the back strap 228 of the right base portion $200^R$ (see FIG. 12a) as will be described below.

A patient, in order to dress him or herself into the left and right base portions $200^L$ and $200^R$, preferably does so by the following steps, as will be understood with general reference to FIGS. 11a and 12a. First the patient forms arm sleeves from the arm straps 214. Then he or she preferably inserts his or her right arm into the sleeve of the right base portion $200^R$ (not illustrated), and following that he or she inserts his or her left arm into the sleeve of the left base portion $200^L$. The order of dressing into the right base portion $200^R$ before the left base portion 200$^L$, is preferred because, the back strap 226 of the left base portion 200$^L$ should preferably overlie the back strap 228 of the right base portion 200$^R$. That way, the hook strips 230 on the inside of the left back strap 226 are alignable to fasten to the outside of the back strap 228 of the right base portion 200$^R$, as shown by FIG. 12a.

An inventive aspect of the strips 230 of the hook material on the left back strap 226 is that, the relative crossing point of the left and right back straps 226 and 228 can be fixed before the patient begins to dress into the garment 200. Thus the patient need not have the help of another person to align the back straps 226 and 228 in a preferred alignment across his or her back. When the patient undresses out of the garment 200, he or she can leave the back straps 226 and 228 attached in any given position so that upon the next use, the back straps 226 and 228 are pre-positioned in the chosen given position.

The patient next grasps the terminal ends of the back straps 226 and 228—the left strap 226 in his or her right hand, the right strap 228 in the left hand—and fastens the back straps 226 and 228 together via the hook patch 216 on the right back strap 228 (compare FIGS. 10 and 11a). The back straps 226 and 228 are adjusted for comfort like a belt by trial and error.

At this point, the patient proceeds to attaching the front straps 222 and 224 in place. FIG. 11a shows the results of this. The patient pulls the terminal end of the right front strap 224 diagonally down to attach underneath his or her left arm pit to the back strap 228 of the base portion 200$^R$ it is common with:—namely, the right base portion 200$^R$. The same procedure is repeated with the left front strap 222 and left back strap 226. FIG. 11a shows the final results from the front of the patient after completion of dressing into the left and right base portions 200$^L$ and 200$^R$. FIG. 12a shows the final results from the rear.

FIGS. 11a through 12b show the attachment and arrangement of the auxiliary straps 202. In the drawings these straps 202 are shown the same size and attached symmetrically opposite to each other. However, this attachment arrangement is shown in the drawings merely for convenience in this description and does not limit the invention because it could be varied as desired for comfort and more effective posture support.

Figure 12B:
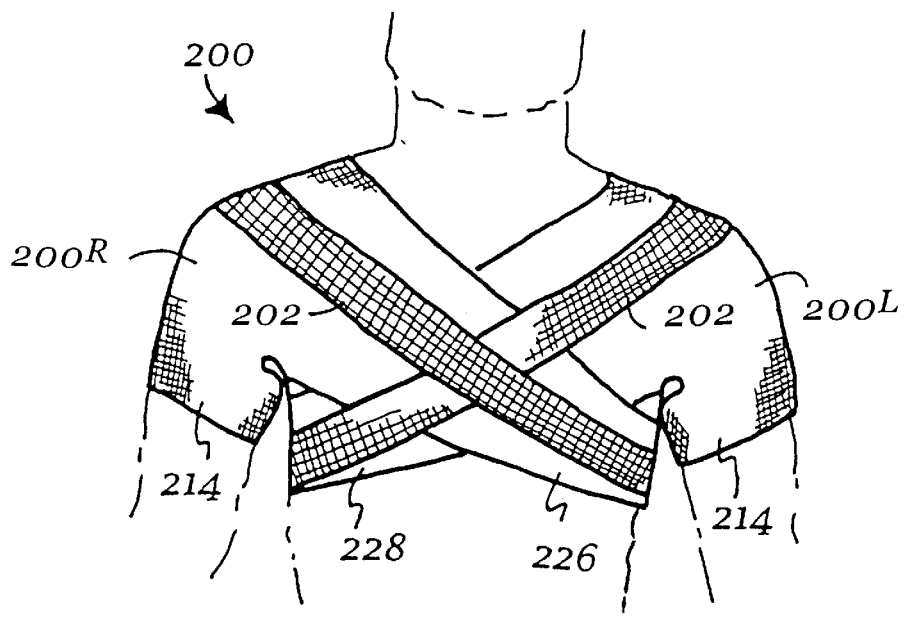
FIG. 12b is a rear perspective view of FIG. 11c.

Attachment of the right auxiliary strap 202 is shown in FIGS. 11a and 11b. It is called the right auxiliary strap because its point of origin begins on the front of the right shoulder, as shown by FIG. 11a. To start with, the patient attaches one end of the right auxiliary strap 202 to a point on the garment 200's right base portion 200$^R$ approximately on the front of the right shoulder, which is shown by FIG. 11a. The opposite end of the auxiliary strap 202, which is shown loose in FIG. 11a, is pulled around the patient's back to come out underneath his or her left arm pit, to attach to the fastened-together back straps 226 and 228 as shown by FIG. 11b. This process is repeated for the left auxiliary strap 202, and the results of this are shown by FIG. 11c. FIG. 12b shows FIG. 11c from the rear. A patient need not designate one or the other of the auxiliary straps 202 as left or right because the straps are generally interchangeable.

Given the foregoing, the FIGS. 11c and 12b orthopedic garment 200 in accordance with the invention is useful for promoting and/or enhancing proper posture with the shoulders relative the spine, and thereby is useful for treating various disorders, malalignments, and/or dysfunctions of the upper extremity.

More particularly, the purpose of the orthopedic garment 200 configured and arranged as shown by FIGS. 11c and 12b is to dynamically support and/or enhance proper posture in a given patient. There are various situations that exist where good posture is required for proper biomechanics and healing. One situation involves treatment of thoracic outlet syndrome, which has been described previously. Also, the inventive support 200 provides posture-enhancing advantages for the "neurologically insulted" patient (who might have had CVA's, strokes and/or other brain-injurious traumas), such as to dynamically support and promote proper posture of their forward-drooping shoulder and spine. Another situation where good posture is required or highly desirable involves cases of thoracic compression fractures, the most common cause of which is the condition of osteoporosis typically limited to elderly patients, mostly women. And still another situation involves spine pathology, which includes treatment of cervical, lumbar and/or thoracic rib dysfunction. Spine pathology also includes treatment of dysfunctions in the temporo-mandibular joint, or, in more everyday language, the jaw.

The temporo-mandibular joint is involved with posture in the upper extremity because the muscles which move the jaw are also partly involved in maintaining correct posture of the jaw relative to the head and neck (the teeth and tongue also participate in this posture work, and nerve endings in the temporo-mandibular joint help guide the head and neck posture and level vision). Correspondingly, the posture of the head and neck affect the proper posture jaw. Put differently, before the posture of the jaw relative to the head and neck can be effectively treated, then preferably the head and neck are supported in a given proper posture.

Inventive aspects of the orthopedic garment 200 of FIGS. 11c and 12b include the following. Preferably the garment 200 can dressed into by the patient alone, without help from another person. Also, the garment 200 directly influences round shoulder posture because the base portions 200$^L$ and 200$^R$ directly encompass the patient's shoulders (FIGS. 11a through 12b), and, in combination therewith, the auxiliary straps 202 actively pull (or induce) the shoulders into (or to assume) a relatively more erect (or proper) posture. The base portions 200$^L$ and 200$^R$ may omit the arm and shoulder portions 212 (see FIG. 10, the omission of which is not shown) because there is less need for frictionally grabbing the skin for this garment 200 to effectively perform its posture supporting/enhancing work, as compared to the need for the FIG. 6 garment 100 to frictionally grab the skin as is important for dynamical scapular or acromio-clavicular stabilization.

Furthermore, the base portions 200$^L$ and 200$^R$ are configured such that, in combination with the arrangements of the auxiliary straps (FIGS. 11c and 12b), the patient is not gripped via a tightly encircled band of elastic material under the arm pit. This avoids compromising (or pinching or compressing) the neuro-vascular bundle under the arm pit. Thus the blood supply to the arm and hand should not be interfered with by the wearing of this orthopedic garment 200 in accordance with the invention.

Further still, the base portions 200$^L$ and 200$^R$ of the orthopedic garment 200 of FIGS. 11c and 12a are advantageously customizable to comfortably fit a given patient size, whether a relatively larger or smaller individual. Additionally, the auxiliary straps 202 dynamically enhance/ support proper posture in accordance with a patient's needs. As a patient's day extends, the patient can loosen or tighten the auxiliary straps 202 in accordance with comfort or in accordance with periods of relative activity and inactivity.

The auxiliary straps 202 give a patient the option of varying the point at which the auxiliary straps cross the patient's back (see FIG. 12b). If the auxiliary straps 202 are crossed at a relatively lower position on the spine, then such a crossing position allows the patient relatively more thoracic extension with scapular retraction, than otherwise. In contrast, if the auxiliary straps 202 are crossed at a relatively higher position on the spine (two different crossing points not shown), then such a higher crossing point enhances scapular retraction more than a lower crossing point.

FIG. 13 shows still another embodiment of the orthopedic garment in accordance with the invention including a base 300 and diverse auxiliary straps 302 and 306. Various portions of the base garment and straps have attached to them patches of hook material 324 of a hook-and-pile fastening system. The FIG. 13 garment 300 is shown resting flat with its outer surface down (not in view, but indicated as 312 in FIG. 14a) and its inner surface 314 up. The base garment 300 is made substantially from Fabri-Foam™ material. This material is breathable and allows ventilation to keep down discomfort due to perspiration. It is thin. It provides a skin-gripping, substantially non-migrating inner surface 314. Its exterior provides a Velcro™ attachable material so that the auxiliary straps can be attached about anywhere. The material is also sufficiently elastic to compress against the skin of or a thin undergarment on the patient to get a sufficient frictional grip on the patient to prevent unwanted migration.

The base garment 300 includes left and right chest (or waist or torso) straps 326 and 328 like those for the FIG. 6 garment 100. It also has a sleeve-forming arm strap 322 for encircling an upper arm of the patient. It further includes a forked down strap 332 which has a point of origin in an arm-and-shoulder portion 316, from which it terminates in a front branch 336 and side branch 338.

In use, the garment 300 is worn by the patient as shown by FIGS. 14a and 14b. The arm strap 322 forms a loop depending from the arm-and-shoulder portion 316 to define a sleeve, and is worn on the involved arm (i.e., the right arm here, or whichever side of the patient that has the given pathology). The opposite torso straps 326 and 328 form a loop or belt around the mid-riff of the patient and fasten together at one side approximately under the front part of the torso of the involved arm of the patient, and below the breasts. The forked down strap 332 extends down from the arm-and-shoulder portion 316 wherein the front and side branches 336 and 338 flank opposite sides of the right breast of the patient, to attach as shown to the band of the connected torso straps 326/328. It is an inventive aspect of the garment 300 that the various straps diverge above or below the breasts of the patient so that the garment is as comfortable for use by female or heavy-breasted patients (male or female) as well as by flat-chested patients.

FIG. 15 is a front perspective view of opposite left and right versions of the base garment 300 of FIG. 13 shown worn by one patient at the same time in order to obtain the equivalence of a bilateral base garment.

Still other inventive aspects of the orthopedic garment 300 relates to its configuration and arrangement so that a patient can preferably dress into it alone, so as not to require attendance by another to dress into it, even with an immobile right (or involved) arm. Preferably, the patient would first form the sleeve via the arm strap 322, but if the patient is not too immobile, he or she might be capable of doing this directly onto his or her arm. However, it still is preferred if the patient, on the supposition that he or she likely is too stiff or immobile to build the sleeve on his or her arm, would build the sleeve before-hand, and then slip his or her left arm into the pre-built sleeve. Irrespective how the patient gets his or her arm into the sleeve, the patient then forms the chest torso loop or belt via the opposite torso straps 326 and 328. Finally, the patient should secure the forked strap 332 as shown. The arm band 322 aside, the other straps fasten in the front of the patient's chest, which can be accomplished even by a patient who has an immobile left arm.

FIGS. 16a though 26c show the attachment and arrangement of the different auxiliary straps. These straps are neoprene or a like resilient material, with hook patches 324 affixed at the opposite ends thereof (see FIG. 13). The auxiliary strap 302 is between approximately 18 to 36 inches (45 to 90 cm) long. The deltoid strap 306 is proportioned as follows:—it is between about 5 to 8 inches (13 to 20 cm) wide, and about 5 to 10 inches (13 to 25 cm) high. Preferably the straps are labeled to allow the patient to choose them correctly from written and/or illustrated instructions.

FIGS. 16a and 16b show application of the deltoid strap 306. Clinical evidence suggests that application of the deltoid strap 306 as shown promotes the proper resting alignment of the scapula and, as importantly, supports the upper arm by way of enhancing proper positioning and gliding of the humeral head (ball) in the scapula's glenoid cavity (socket). It gives additional support to the muscles connected to and responsible for moving the scapula, and thereby (i) relieves tension in those muscles as well as (ii) obviates compensation from accessory muscles and thus prevents secondary pathologies or muscle strains as resultant from the base or primary pathology.

FIGS. 17a and 17b show application of the auxiliary strap 302. Clinical evidence suggests that it enhances the positioning of and pull on the scapula ordinarily achieved by the middle and lower fibers of a healthy trapezius muscle 48 (see, e.g., FIG. 3). The auxiliary strap 302 preferably is located with one end approximately on the front of the acromion process of the scapula, as shown in FIG. 17a. From this origin, the auxiliary strap 302 is looped behind the back of the patient and under the uninvolved arm pit, as shown in FIG. 17b, to be secured to the base garment 300 as shown with reference back to FIG. 17a again.

In commonly-owned, commonly-invented U.S. Pat. No. 5,857,990—Maas, the straps 102 and 302 were previously relied on to provide uni-lateral (eg., for one side only) trapezius support. Said U.S. Pat. No. 5,857,990—Maas, is hereby incorporated in full by this reference to it. In the present invention where the straps 102 and 302 are preferably utilized in a bi-lateral arrangement as shown by straps 202 in FIG. 12b. Hence this demonstrates the adaptability of the inventive base garment and strap system for adding more straps and addressing multiple symptoms or indications in one patient. In FIG. 12b, the two straps 202 cooperate to dynamically support and/or enhance proper posture in a given patient. Bi-lateral wearing of base garments 100 or 300 to arrange straps 102 or 302 in bi-lateral fashion like FIG. 12b, demonstrates the adaptability of the inventive base garment and strap system. That is, by simply changing the strap system from one of unilateral wearing to bi-lateral wearing affords the patient to re-direct which symptoms or indications are being addressed. As previously mentioned, there are various situations that exist where good posture is required for proper biomechanics and healing. One situation involves treatment of thoracic outlet syndrome, which has been described previously. Another situation involves thoracic compression fractures, the most common cause of which is the condition of osteoporosis typically limited to elderly patients, mostly women. And still another situation involves spine pathology, which includes treatment of cervical, lumbar and/or thoracic rib dysfunction. Spine pathology also includes treatment of dysfunctions in the temporo-mandibular joint, or, in more everyday language, the jaw.

It is an aspect of the foregoing base garment and strap system in accordance with the invention, that it is possible for a patient to dress into it and apply and adjust the straps alone, without aid from others. In order to achieve this aspect, the ends of the straps which attach on the back of the patient (or in otherwise unreachable places) ought to be pre-affixed before the patient dresses into the base garment 300. As an aid for this, the clinical or treating physical therapist might mark directly onto the base garment 300 and/or straps the locations where the various straps attach. Alternatively, the awkward ends of the straps might be sewn or otherwise semi-permanently affixed to the base garment 300 and/or each other (in instances where one strap attaches atop another). Either way, the object is to achieve consistency for where the patient starts with the first-attached ends of the straps to the base garment. If done properly, then all the tag ends (e.g., loose ends) of the straps ought to secure or fasten in front of the patient, where he or she can do this alone in order to complete application/adjustment of the straps.

FIGS. 7, 11a and 13 depict alternative arrangements of a base garment 100, 200 and/or 300 for attachment of various auxiliary straps 102, 202, 302, and 306 for purposes described above. In the above-incorporated U.S. Pat. No. 5,857,990—Maas, the FIGS. 7 and 13 base garment(s) 100 and 300 were disclosed more in connection with scapular stabilization than the FIGS. 11a base garment 200, which was more or less disclosed in connection with posture support and/or enhancement. The base garments 100, 200 and/or 300 of FIGS. 7, 11a and 13 are interchangeable substitutes for one another, and each works effectively in performing the functions that have been more particularly described in connection with one of the others.

Figure 18:
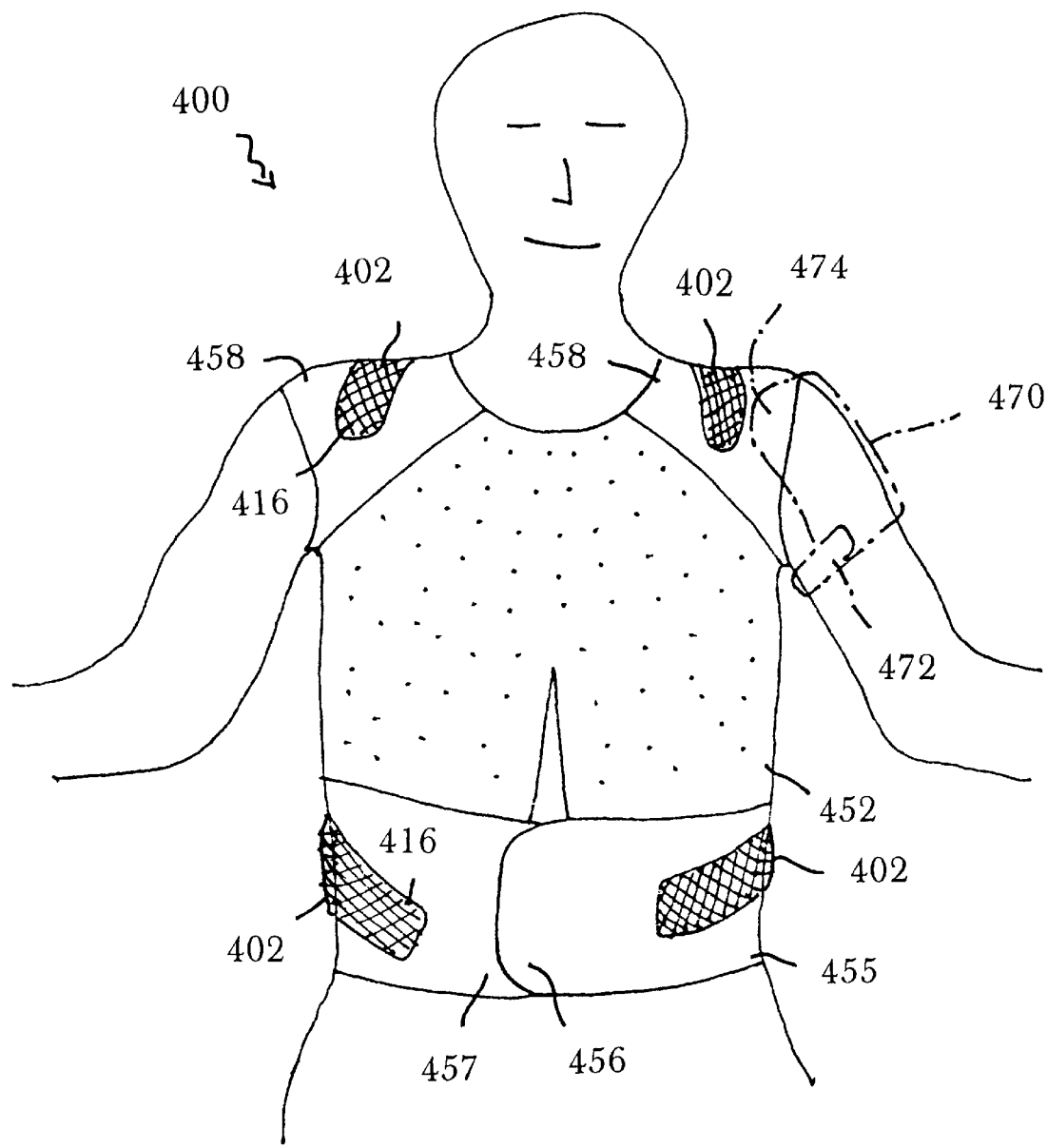
FIG. 18 is a front perspective view of still a further orthopedic garment in accordance with the invention for dynamically enhancing proper posture in the upper extremity; and, FIG. 19 is a rear perspective view of the FIG. 18.
Figure 19:
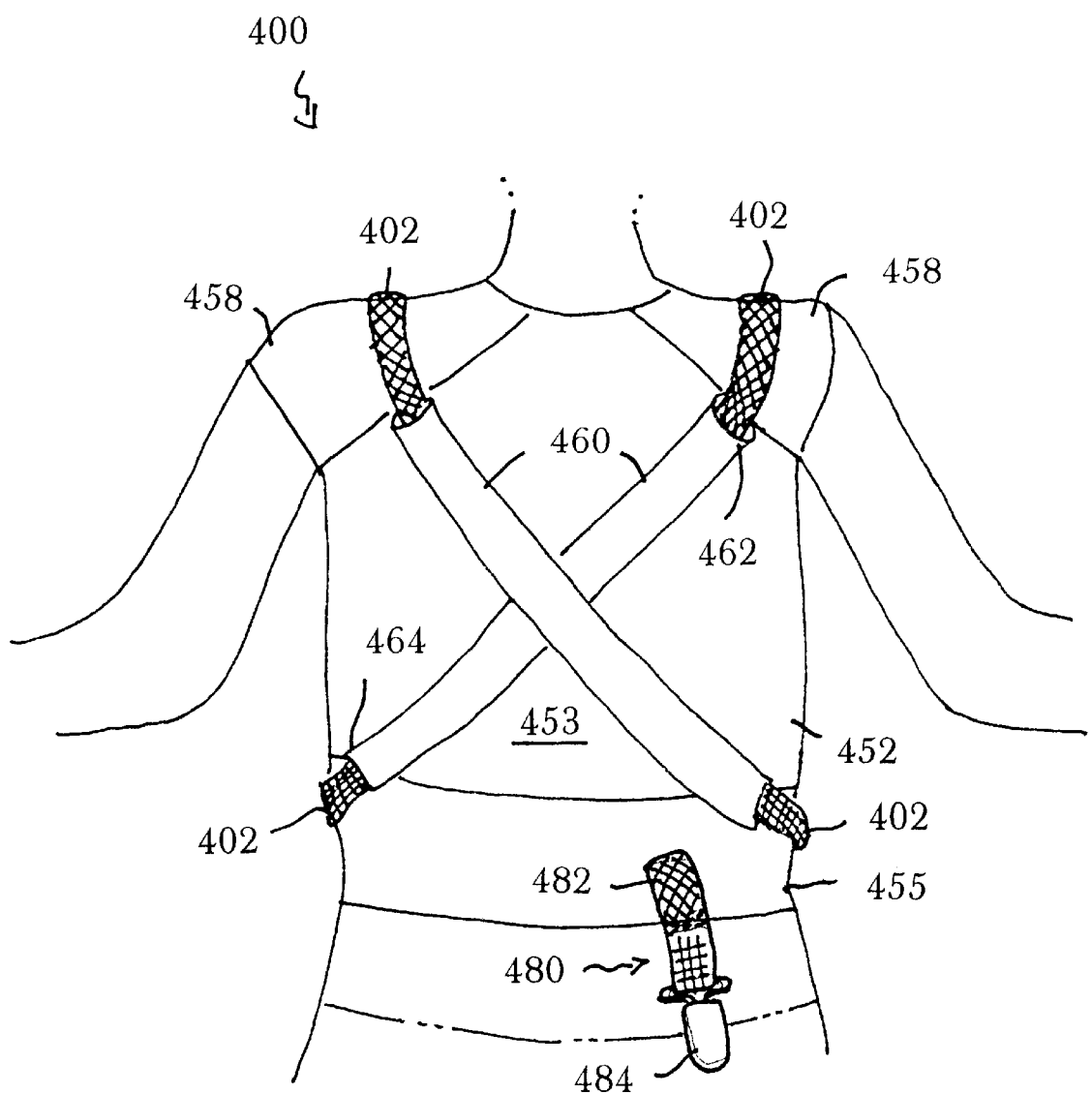

FIG. 18 is a front perspective view of still a further orthopedic garment 400 in accordance with the invention for dynamically enhancing proper posture in the upper extremity. FIG. 19 is a rear perspective view of the FIG. 18.

FIGS. 18 and 19 show an elastic base garment 400 combined with a system of elastic halter straps 402. The base garment 400 preferably comprises a stocking-like tube 452 interconnecting a waist band 455 with a pair of shoulder pads 458 or shoulder-draping portions. Thus the base garment 400 can take the format of a generally sleeveless, generally collarless, waist-length body stocking, or something like a camisole. The shoulder areas or pads 458 are preferably not actually sleeveless but roll down the shoulder a part of the way as shown by the drawings.

The shoulder pads 458 and waist band 455 can be made of material as previously described above. That is, the shoulder pads 458 and waist band 455 can have diverse inner and outer surfaces wherein the inner surface is adapted for high friction contact with the patient's skin or a thin undergarment worn by the patient, the outer surface being provided with said hook-fastener securing areas. The stocking material 452 is preferably much lighter and thinner but also elastic. The stocking material's inner surface is likewise preferably adapted for high friction contact with the patient's skin or a thin undergarment worn by the patient.

FIG. 19 shows that the base garment 400 is provided with a pair of diagonally-crossing casements 460 that may be sewn or adhesively bonded or otherwise attached directly to the back part 453 of the stocking material 452. The casements 460 extend between upper exits 462 at or below the shoulder pads 458 and lower exits 464 at or above the waist band 455. The casements 460 cross diagonally such that each casement 460 extends up from one side of the waist to the shoulder on the opposite side. The casements 460 may be made of substantially the same light material as the stocking 452.

The halters 402 are elastic, and are provided with hook-fastener tag ends 416. The halter's tag ends 416 are preferably enlarged to make it difficult that the tag ends 416 be inadvertently retracted in through any casement exit 462 or 464. In use, the halter's hook-fastener tag ends 416 are secured to the base garment's hook-fastener securing areas 455 and 458 such that the following is accomplished. That is, one of the halters 402 is arranged to supply tension between an origin on the right one of the shoulder pads 458 and a termination on the waist band 455 approximately on the left side, as the other of the halters 402 supplies tension between an origin on the left one of the shoulder pads 458 and another termination on the waist band 455 approximately on the right side. More particularly, the origins are located over the front or "anterior" of the patient's shoulders or, more preferably still, over the acromion process. The terminations can be secured in any various place on the waist band 455 ranging from the sides to over the abdomen.

In fact, it is supposed that during a given instance of wearing the orthopedic garment 400 and halters 402, the patient is likely to adjust the halters 402 according to comfort or need. Preferably the halter ends 416 which are moved to accomplish adjustment are the lower ends attached to the waist band 455. For example, while standing, the patient may desire to tighten the halters 402 after having stood up from sitting, and vice versa.

The halters 402 are stretched across courses which from the origins on the shoulder pads 458, arch behind the patient's shoulders over his or her trapezius muscles, diagonally down the patient's back to the side of the waist on the opposite side as the shoulder of the origin, for attachment to the waist band 455 in any of various suitable places as described. Thus the halters 402 provide diagonally-crossing filaments of tension across the patient's back in order to oppose slouching and thereby enhance proper erect posture. The casements 460 provide support or constraint to, or afford maintenance of the courses of the halters 402 despite the patient's twisting, bending or contortions.

It's not so much that the intended patients will want to perform acrobatics. But rather, even if the patients have diminished posture function, they are not going to sit, stand or walk like straight-ahead focused zombies. These patients will sometimes flex sideways and twist in the back, as someone does when he or she reaches around behind themselves to grab something about at the back of their knees. It is an object of the invention to provide posture support for such patients even when the patient is in motion, and not just when at rest or certainly not merely when plainly immobilized. Put differently, one object of the invention is to liberate patients to pursue leading normal lives with freedom from un-comfortable confinement in stiff traction.

It is a preferred option that the waist band 455 is produced with overlapping belt ends 456 and 457, one of which belt 456 ends is provided with hook fasteners to allow releasable tightening or slackening of the waist band 455 around the patient's waist. The stocking portion 452 is slit above where the belt ends 456 and 457 overlap to accommodate pleating (if not eliminate pleating).

The objects of the invention are best achieved if the waist band 455 truly remains stationary at the given elevation around the patient's torso which the waist band 455 is originally set. It would be problematical if the waist band 455 crept up the patient's back. That is, it would be problematical if the tension which is purposely loaded into the stretched halters 402, is unloaded by pulling up the waist band 455, and hence shortening the distance between the attached tag ends 416.

Among the ways which the waist band 455 is anchored stationary include the following. The waist band 455 is exceptionally wide or broad, eg., it has widely spaced upper and lower edges. Since the side of the waist band 455 that touches the skin is grabby, the increased breadth of the waist band 455 increases the surface area of the waist band 455 frictionally grabbing the patient's skin. Also, the increased bandwidth of the waist band 455 in combination with its elasticity, increases the band- or girdle-width on the patient's waist which the waist band can "latch" onto, and mechanically fasten itself to the patient's contours.

That is, for a such patient having an hourglass waist, the waist band 455 girdles "in" at the waist and latches itself there. In contrast, for a given patient having a full figure, the waist band 455 might girdle "out" at the waist but nevertheless latch onto this given patient as well as the other patient with the hourglass waist.

FIG. 19 shows an auxiliary means of holding the waist band 455 down, comprising a hold-down strap 480. The hold-down strap 480 is elastic in its mid-span, and extends between an upper hook-fastener end 482 and a lower garter-clip end 484. The upper hook fastener end 482 attaches to anywhere on the waist band 455 that provides hook-fastener securing areas (eg., pile). In the preferred embodiment, substantially the entire waist band 455 has an outer surface of pile material that allows fastening of hook fastener(s) 482. The lower garter-clip end 484 enables attachment to the waist of the underwear of the patient (whether male or female). By these means, the hold-down strap 480 provides additional anchoring power to the inventive waist band 455. Whereas the drawings only show a single hold-down strap 480 in the rear view of FIG. 19, the invention accommodates the use of as many hold-down straps 380 as the patient desires to wear. The patient may want to wear two hold-downs 480 in the back only, or two in back and two in front, whatever. The illustration of just a single hold-down strap 480 in FIG. 19 is provided for sake of illustration only and is not limiting to the invention.

FIG. 18 shows that the foregoing orthopedic garment 400 might further include the following enhancement. That is, there might be provided an elastic tension-relieving sleevelet 470 for securing to the base garment 400. Such a sleevelet 470 would include an upper-arm encircling portion 472 for securing to the patient's upper arm. To do this, the sleevelet 472 would have VELCRO™ securing areas to allow adjustment of strap 472. The sleevelet 470 would also include one or more spaced attachment points 474 featuring hook fasteners in order to allow the attachment points 474 to fasten onto one or the other of the shoulder-draping portions 458 of the base garment 400.

Given the above, the tension-relieving sleevelet 470 provides relief to the tension in the muscles and nerves connected to and responsible for moving the scapula as well as obviates compensation from accessory muscles such as ones that move the upper arm. It will be recognized that the tension-relieving sleevelet 470 substantially overlies the deltoid muscle.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. An orthopedic method for dynamically enhancing proper posture of a patient, comprising the steps of:

applying to the patient an elastic base-garment comprising left and right shoulder pads, a waist band, and a stocking portion interconnecting the shoulder pads and waist band;

providing the shoulder pads and waist band with hook-fastener securing areas;

providing a pair of diagonally-crossing casements on the back of the garment, the casements extending between catercorner exits including upper exits at or below the shoulder pads and lower exits at or above the waist band;

providing a pair of elastic halters with hook-fastener tag ends;

pairing the halters with the casements and feeding the halters therethrough;

securing the halter's hook fasteners to the base garment's hook-fastener securing areas such that one halter supplies tension between an origin on the front of the right shoulder pad and a termination on the waist band either on the left side or over the abdomen, by a course stretching over the patient's trapezius and then diagonally across the back to around the patient's left side, as the other halter supplies tension between an origin on the front of the left shoulder pad and another termination on the waist band either on the right side or over the abdomen, by a course stretching over the patient's trapezius and then diagonally across the back to around the patient's right side;

wherein the halters provide diagonally-crossing filaments of tension across the patient's back in order to oppose slouching and thereby enhance proper erect posture, as the casements afford maintenance of the courses of the halters despite such contortions as concurrent twisting and bending sideways.

2. The orthopedic method of claim 1, further comprising providing the waist band and shoulder pads with diverse inner and outer surfaces wherein the inner surface is adapted for high friction contact with the patient's skin or a thin undergarment worn by the patient, the outer surface being provided with said hook-fastener securing areas.

3. The orthopedic method of claim 2, wherein the stocking portion is provided with an inner surface that is adapted for high friction contact with the patient's skin or a thin undergarment worn by the patient.

4. The orthopedic method of claim 1, wherein the waist band further includes overlapping belt ends, one of which belt ends is provided with hook fasteners to allow releasable tightening or slackening of the waist band around the patient's waist.

5. The orthopedic method of claim 4, wherein the stocking portion is slit above where the belt ends overlap to accommodate pleating.

6. The orthopedic method of claim 1 wherein the hook-fastener tag ends of the pair of halters are enlarged to make difficult inadvertent retraction in through any casement exit.

7. The orthopedic method of claim 1 wherein the orthopedic garment is one of collarless and sleeveless, or collarless and substantially sleeveless except including at least part of a shoulder cap.

8. The orthopedic method of claim 1, further comprising:
providing an elastic tension-relieving sleevelet for securing to the base garment, which sleevelet includes an upper-arm encircling portion for securing to the patient's upper arm, and includes one or more spaced attachment points provided with hook fasteners that allow fastening to one or the other shoulder-draping portions of the base garment;
wherein the tension-relieving sleevelet provides relief to the tension in the muscles connected to and responsible for moving the scapula as well as obviates compensation from accessory muscles such as ones that move the upper arm.

9. The orthopedic method of claim 8 wherein the tension-relieving sleevelet substantially overlies the deltoid muscle.

10. An orthopedic method for dynamically enhancing proper posture of a patient, comprising the steps of:
applying to the patient an elastic base-garment comprising left and right trapezius-draping portions, a waist band, and intermediary material for extending between and operatively interconnecting the trapezius-draping portions and the waist band;
providing at least the waist band with hook-fastener securing areas;
providing the intermediary material with a dorsal span;
attaching a pair of diagonally-crossing casements to the dorsal span, the casements extending between cater-corner exits including upper exits at or below the trapezius-draping portions and lower exits at or above the waist band;
providing a pair of elastic halters which have one and another tag ends, and providing at least the other tag end with hook fasteners;
pairing the halters with the casements and feeding the halters therethrough;
coupling the halters to the base garment such that one halter's one end is attached to an origin on the front of the right trapezius-draping portion as said one halter's other end having the hook-fasteners is secured to a termination on the waist band either at the left side or over the abdomen, by a course stretching over the patient's trapezius and then diagonally across the patient's back to around the patient's left side, as the other halter's one end is attached to an origin on the front of the left trapezius-draping portion as said other halter's other end having the hook-fasteners is secured to another termination on the waist band either at the right side or over the abdomen, by a course stretching over the patient's trapezius and then diagonally across the patient's back to around the patient's right side;
wherein the halters provide diagonally-crossing filaments of tension across the patient's back in order to oppose slouching and thereby enhance proper erect posture, as the casements afford dynamic maintenance of the courses of the halters despite such contortions as concurrent twisting and sideways bending.

11. The orthopedic method of claim 10, further comprising providing the waist band and trapezius-draping portions with diverse inner and outer surfaces wherein the inner surface is adapted for high friction contact with the patient's skin or a thin undergarment worn by the patient, the outer surface being provided with said hook-fastener securing areas.

12. The orthopedic method of claim 10, wherein the intermediary material is attached to the waist band and the trapezius-draping portions by sewn seams or a bonding agent, and the intermediary material comprises a substantially different material from the material of the waist band and the trapezius-draping portions.

13. The orthopedic method of claim 10, further comprising one or more auxiliary hold-down straps that extend between an upper hook-fastener end for securing to the base garment's waist band, and, a lower garter-clip end for securing to the waist of the patient's underwear, whereby the auxiliary hold-down straps provide auxiliary support for anchoring the base-garment's waist band from creeping up on the patient.

14. The orthopedic method of claim 10 wherein the waist band further includes overlapping belt ends, one of which belt ends is provided with hook fasteners to allow releasable tightening or slackening of the waist band around the patient's waist.

15. The orthopedic method of claim 10 wherein the orthopedic garment is one of collarless, sleeveless, or substantially sleeveless except including at least a partial shoulder cap.

16. The orthopedic method of claim 10, further comprising:
providing an elastic tension-relieving sleevelet for securing to the base garment, which sleevelet includes an upper-arm encircling portion for securing to the patient's upper arm, and includes one or more spaced attachment points provided with hook fasteners that allow fastening to one or the other trapezius-draping portions of the base garment;
wherein the tension-relieving sleevelet provides relief to the tension in the muscles connected to and responsible for moving the scapula as well as obviates compensation from accessory muscles such as ones that move the upper arm.

17. The orthopedic method of claim 16 wherein the tension-relieving sleevelet substantially overlies the deltoid muscle.

18. An orthopedic method for dynamically enhancing proper posture of a patient, comprising the steps of:
applying to the patient an elastic base-garment comprising left and right trapezius-draping portions, a waist band, and intermediary material for extending between and operatively interconnecting the trapezius-draping areas and the waist band;
providing the trapezius-draping portions and waist band with hook-fastener securing areas;
providing a pair of elastic halters with hook-fastener tag ends;
securing the halter's hook fasteners to the base garment's hook-fastener securing areas to have the halters crossing diagonally across the patient's back, such that one halter supplies tension between an origin on the front of the right trapezius-draping portion and a termination on the waist band either on the left side or over the abdomen, by a course arching over behind the right shoulder and then diagonally across the patient's back to around the patient's left side, as the other halter supplies tension between an origin on the front of the left trapezius-draping portion and another termination on the waist band either on the right side or over the abdomen, by a course arching over behind the left shoulder and then diagonally across the patient's back to around the patient's right side;

providing the intermediary material with a dorsal span;

providing halter-stationing means for stationing the intersection where the halters cross in the back to a given station on the dorsal span;

wherein the halters provide diagonally-crossing filaments of tension across the patient's back in order to oppose slouching and thereby enhance proper erect posture, as the halter-stationing means affords maintenance of the courses of the halters despite such contortions as concurrent twisting and sideways bending.

19. The orthopedic method of claim 18 wherein the halter-stationing means comprises diagonally-crossing casements attached to the dorsal span.

20. The orthopedic method of claim 18 wherein the halter-stationing means comprises fastener means for fastening the intersection of the crossing halters to the given station on the dorsal span.

* * * * *